(12) United States Patent
Endo et al.

(10) Patent No.: US 10,537,247 B2
(45) Date of Patent: Jan. 21, 2020

(54) INFORMATION PROCESSING APPARATUS, METHOD, AND PROGRAMMED STORAGE MEDIUM, FOR CALCULATING RANGES OF REGIONS OF INTEREST OF SCANNED OR OTHER IMAGES

(71) Applicant: CANON KABUSHIKI KAISHA, Tokyo (JP)

(72) Inventors: Takaaki Endo, Urayasu (JP); Kiyohide Satoh, Kawasaki (JP); Ryo Ishikawa, Kawasaki (JP); Takuya Ishida, Tokyo (JP); Kazuhiro Miyasa, Narashino (JP)

(73) Assignee: Canon Kabushiki Kaisha, Tokyo (JP)

( * ) Notice: Subject to any disclaimer, the term of this patent is extended or adjusted under 35 U.S.C. 154(b) by 49 days.

(21) Appl. No.: 15/820,251

(22) Filed: Nov. 21, 2017

(65) Prior Publication Data
US 2018/0092537 A1    Apr. 5, 2018

Related U.S. Application Data

(62) Division of application No. 14/110,080, filed as application No. PCT/JP2012/002227 on Mar. 30, 2012, now Pat. No. 9,867,541.

(30) Foreign Application Priority Data

Apr. 6, 2011 (JP) .................. 2011-084495
Jan. 18, 2012 (JP) .................. 2012-008205
Feb. 24, 2012 (JP) .................. 2012-038883

(51) Int. Cl.
*G06K 9/00* (2006.01)
*A61B 5/00* (2006.01)
(Continued)

(52) U.S. Cl.
CPC .............. *A61B 5/0037* (2013.01); *G06T 7/33* (2017.01); *G06T 11/00* (2013.01); *G06T 19/00* (2013.01);
(Continued)

(58) Field of Classification Search
CPC ..... A61B 5/0037; G06F 19/321; G06T 11/00; G06T 19/00; G06T 2200/24;
(Continued)

(56) References Cited

U.S. PATENT DOCUMENTS

| 7,204,807 B2* | 4/2007 | Tsoref | A61B 5/107 382/128 |
| 2005/0004451 A1* | 1/2005 | Vilsmeier | A61B 90/36 600/426 |

(Continued)

*Primary Examiner* — Bhavesh M Mehta
*Assistant Examiner* — Ian L Lemieux
(74) *Attorney, Agent, or Firm* — Canon U.S.A., Inc. IP Division

(57) ABSTRACT

An information processing apparatus according to the present invention is configured to project a given region (e.g., region of interest or lesion of interest) in a three-dimensional image (e.g., MRI image or X-ray CT image) onto a plane including a two-dimensional image (e.g., ultrasonic image) of an object, and cause a display unit to display an error range caused by projection (range where a corresponding region of the region of interest in the two-dimensional image may exist, also referred to as a search range) including the projected region in such a manner that the error range is overlaid on top of the two-dimensional image.

Therefore, a user is able to efficiently search for the corresponding region in the two-dimensional image which corresponds to the region of interest in the three-dimensional image.

17 Claims, 17 Drawing Sheets

(51) Int. Cl.
*G06T 7/33* (2017.01)
*G06T 11/00* (2006.01)
*G06T 19/00* (2011.01)
*G06F 19/00* (2018.01)
*G16H 30/20* (2018.01)

(52) U.S. Cl.
CPC ........ *G06F 19/321* (2013.01); *G06T 2200/24* (2013.01); *G06T 2207/10081* (2013.01); *G06T 2207/10088* (2013.01); *G06T 2207/10132* (2013.01); *G06T 2210/41* (2013.01); *G16H 30/20* (2018.01)

(58) Field of Classification Search
CPC . G06T 2207/10081; G06T 2207/10088; G06T 2207/10132; G06T 2210/41; G06T 7/33; G16H 30/20
See application file for complete search history.

(56) References Cited

U.S. PATENT DOCUMENTS

| | | | | |
|---|---|---|---|---|
| 2007/0015995 | A1* | 1/2007 | Lang | A61B 5/055 600/407 |
| 2007/0263924 | A1* | 11/2007 | Kochi | G01B 11/24 382/154 |
| 2008/0123910 | A1* | 5/2008 | Zhu | A61B 90/36 382/128 |
| 2008/0262345 | A1* | 10/2008 | Fichtinger | A61B 6/504 600/426 |
| 2011/0184684 | A1* | 7/2011 | Li | A61B 90/36 702/94 |
| 2015/0070469 | A1* | 3/2015 | Yoshibayashi | G06T 19/00 348/46 |
| 2015/0363907 | A1* | 12/2015 | Satoh | G06T 7/30 382/289 |
| 2015/0371361 | A1* | 12/2015 | Kim | G06T 3/0068 382/128 |
| 2017/0206670 | A1* | 7/2017 | Miyasa | G06T 7/11 |
| 2017/0354342 | A1* | 12/2017 | Ben-Yishai | A61B 34/20 |
| 2018/0040147 | A1* | 2/2018 | Alhrishy | A61B 6/02 |

* cited by examiner

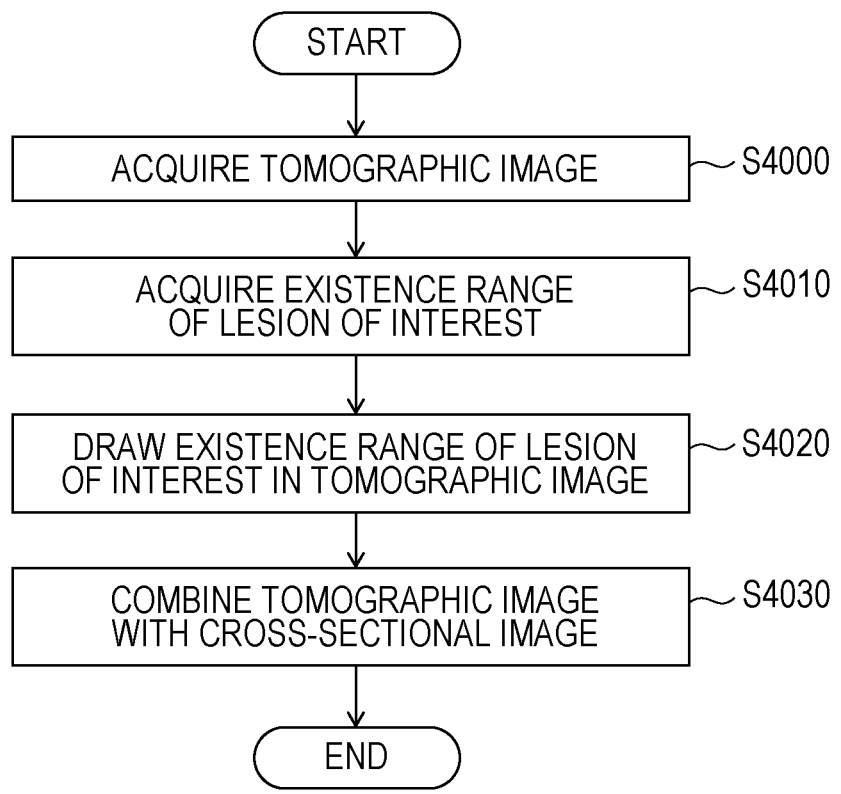

INFORMATION PROCESSING APPARATUS, METHOD, AND PROGRAMMED STORAGE MEDIUM, FOR CALCULATING RANGES OF REGIONS OF INTEREST OF SCANNED OR OTHER IMAGES

CROSS-REFERENCE TO RELATED APPLICATIONS

This is a divisional application of, and claims the benefit of, U.S. patent application Ser. No. 14/110,080 filed Oct. 4, 2013 (now U.S. Pat. No. 9,867,541), which is a 371 National Phase filing of International Application No. PCT/JP2012/002227 filed on Mar. 30, 2012, which claims the benefit of Japanese Patent Application No. 2011-084495, filed Apr. 6, 2011, Japanese Patent Application No. 2012-008205, filed Jan. 18, 2012, and Japanese Patent Application No. 2012-038883, filed Feb. 24, 2012. Each of U.S. patent application Ser. No. 14/110,080, International Application No. PCT/JP2012/002227, Japanese Patent Application No. 2011-084495, Japanese Patent Application No. 2012-008205, and Japanese Patent Application No. 2012-038883 is hereby incorporated by reference herein in its entirety.

TECHNICAL FIELD

The present invention relates to an information processing apparatus for efficiently searching for corresponding regions of a region of interest in images having different imaging conditions such as modalities, imaging positions, and imaging dates and times.

BACKGROUND ART

In the medical field, doctors display medical images of objects (three-dimensional image data including tomographic images indicating three-dimensional information about the inside of the object) on monitors and interpret (or read) the displayed images to diagnose lesions. Examples of medical image collection devices (hereinafter referred to as "modalities") for use in medical imaging include an ultrasonic diagnostic imaging apparatus, a magnetic resonance imaging (MRI) apparatus, and an X-ray computed tomography (CT) apparatus.

The observation of a medical image captured by an individual modality is not sufficient for correct diagnosis of the state of a lesion. Therefore, attempts have been made to correctly diagnose the state of a lesion by comparing corresponding regions of the lesion in medical images captured by a plurality of modalities or in medical images captured at different dates and times.

In order to use a plurality of kinds of medical images for diagnosis, it is important to identify (or associate) corresponding regions of a lesion or the like in the respective medical images. Since it is difficult to automatically identify such regions by using image processing due to factors such as different modalities and object deformation, an operator such as a doctor generally performs a manual operation for identifying the regions while viewing the images. The operator searches for and identifies, while viewing an image of a lesion of interest to be focused on which has been pointed out in one medical image (hereinafter referred to as the "reference image"), a corresponding region of the lesion (hereinafter referred to as the "corresponding lesion") in another medical image (hereinafter referred to as a "target image") on the basis of similarity in the shape of the lesion, the appearance of the surroundings of the lesion, and other properties. If an apparatus for presenting a medical image has the function of estimating the position of the corresponding lesion represented in the coordinate system of the target image from the position of the lesion of interest in the coordinate system of the reference image and presenting the estimated position, the operator is able to search for the corresponding lesion on the basis of the estimated position.

Accordingly, attempts have been made to measure the position and posture of an ultrasonic probe to determine the relationship between the coordinate system of the target image, or an ultrasonic tomographic image, and the coordinate system of the reference image, and to estimate the position of the corresponding lesion in the coordinate system of the ultrasonic tomographic image (ultrasonic coordinate system) to navigate the probe. For example, PTL 1 discloses that the distance and direction from the current ultrasonic tomographic image to the center of a target (lesion of interest) set in a reference image (cross-sectional image of a three-dimensional image obtained by an X-ray CT apparatus, an MRI apparatus, or the like) are calculated and a three-dimensional arrow image and numerical values based on the calculated distance and direction are displayed. Thus, the operator is able to visually determine the distance from the current ultrasonic tomographic image to the target, and therefore easily determine a correspondence (positional relationship) between the reference image and the ultrasonic tomographic image.

PTL 2 discloses that when a selected image tracking point (lesion of interest) is given from a previously acquired ultrasonic tomographic image (volume or slice), a square whose size and color are based on the distance and direction from the currently acquired ultrasonic tomographic image is displayed as an in-plane indicator on top of the currently acquired ultrasonic tomographic image. Therefore, when counting the number of nodules in the thyroid, the number of metastases in the liver, or the number of other items, a user can determine whether the current visualized structure is newly identified or has already been identified and counted even if the angle or location of the probe on the object changes.

CITATION LIST

Patent Literature

[PTL 1]
Japanese Patent Laid-Open No. 2008-246264
[PTL 2]
Japanese Patent Laid-Open No. 2008-212680

SUMMARY OF INVENTION

The accuracy with which the position and posture of the ultrasonic probe are measured is not perfect, and the shape of the object may differ between when the reference image is captured and when the ultrasonic tomographic image is captured. Therefore, an estimated position of the corresponding lesion in the coordinate system of the ultrasonic tomographic image may include an error, and may be deviated from the actual position of the corresponding lesion.

However, the distance and direction based indicators disclosed in PTL 1 and PTL 2 do not take such positional deviation into account. Depending on the degree of positional deviation, a user may not be able to identify (or find) the actual corresponding lesion even on the basis of the indicators. Therefore, the user has to search for the actual corresponding lesion through the entire ultrasonic tomographic image, and searching efficiency becomes low.

In an aspect of the present invention, an information processing apparatus includes a two-dimensional image acquisition unit and a display control unit. The two-dimensional image acquisition unit is configured to acquire a two-dimensional image of an object. The display control unit is configured to cause a display unit to display an error range in such a manner that the error range is overlaid on top of the two-dimensional image. The error range includes a projected region obtained by projecting a given region in a three-dimensional image of the object onto a plane including the two-dimensional image, and is caused by the projection.

According to the present invention, it is possible to project a given region (e.g., region of interest or lesion of interest) in a three-dimensional image (e.g., MRI image or X-ray CT image) onto a plane including a two-dimensional image (e.g., ultrasonic image) of an object. It is also possible to cause a display unit to display an error range caused by the projection (range where a corresponding region of the region of interest in the two-dimensional image may exist, also referred to as a search range) including the projected region in such a manner that the error range is overlaid on top of the two-dimensional image. This enables a user to determine a search range within which the actual corresponding region in the two-dimensional image is searched for, and therefore to efficiently search for and identify the actual corresponding region.

BRIEF DESCRIPTION OF DRAWINGS

FIG. 4 is a flow diagram illustrating a processing procedure for combining images in a search mode in the information processing apparatus according to the second embodiment.

DESCRIPTION OF EMBODIMENTS

Exemplary embodiments of an information processing system (information processing apparatus) according to the present invention will be described in detail hereinafter with reference to the accompanying drawings. It is to be noted that the present invention is not limited to the following embodiments.

First Embodiment

An information processing apparatus according to a first embodiment is configured to project a certain region (e.g., a region of interest or a lesion of interest) in a three-dimensional image (e.g., an MRI image or an X-ray CT image) onto a plane including a two-dimensional image (e.g., an ultrasonic image) of an object, and to display an error range caused by the projection described above (a range where the corresponding region of the region of interest in the two-dimensional image may exist, also referred to as a search range) including the projected region, on top of the two-dimensional image on a display unit. This enables a user to determine a search range within which the actual corresponding region is searched for in the two-dimensional image, and to efficiently search for and identify the actual corresponding region.

This embodiment provides a technique based on the projection described above. Specifically, the projection described above allows a region corresponding to the given region to be continuously displayed on top of the two-dimensional image of the object unless errors are caused by the projection. However, due to, for example, an error caused by coordinate transformation described below, a region corresponding to the given region may not necessarily be displayed on top of the two-dimensional image of the object. Displaying an error range on top of a two-dimensional image allows a user to easily search for a region corresponding to a given region.

Figure 6A:
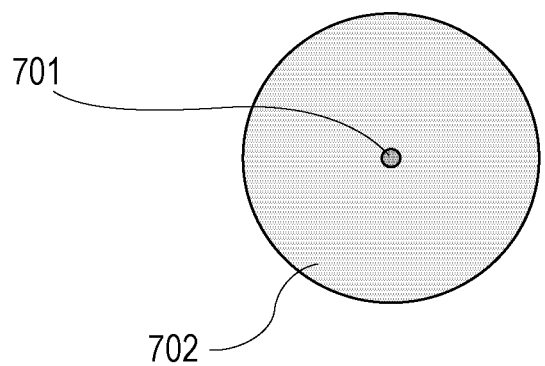
FIG. 6A is diagram illustrating an example of a first region and a second region.
Figure 6B:
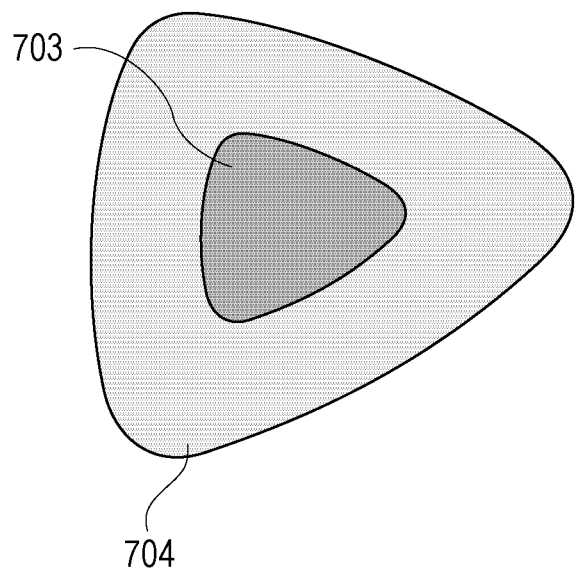
FIG. 6B is diagram illustrating another example of a first region and a second region.

Here, the position of a given region may undergo coordinate transformation (association, position alignment) from the three-dimensional coordinate system of the three-dimensional image to the three-dimensional coordinate system of the two-dimensional image (e.g., the reference coordinate system of a position and posture sensor). Therefore, the error range caused by the projection can be calculated on the basis of an error caused by the coordinate transformation. In addition, the error range caused by the projection can be calculated by setting in a three-dimensional image a region (second region) that is larger than a given region (first region) and that includes the given region and then performing coordinate transformation of the position of the region (second region). The size of the second region may be set on the basis of an error caused by coordinate transformation. For example, as illustrated in FIG. 6A, if a first region 701 is defined as a point having no magnitude, a second region 702 may be a sphere centered on the first region 701 and having a radius equal to an error caused by coordinate transformation. Furthermore, as illustrated in FIG. 6B, if a first region 703 is defined as a closed region having a magnitude, a second region 704 may be a region surrounded by a closed curve defined so that the distance between the closed curve and the nearest neighbor of the first region 703 is equal to an error caused by coordinate transformation.

Figure 1:
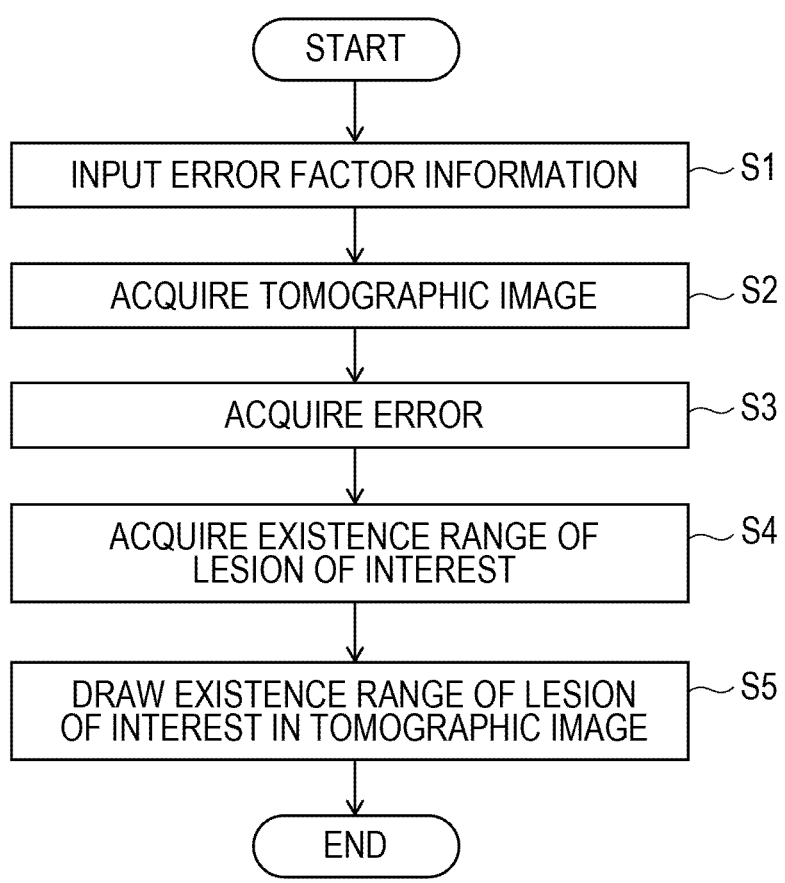
FIG. 1 is a flow diagram illustrating a processing procedure of an information processing apparatus according to a first embodiment.

Next, the information processing system according to this embodiment will be described with reference to FIG. 1. FIG. 1 is a flow diagram illustrating a processing procedure of an information processing apparatus according to this embodiment.

First, in step S1, an error acquisition unit inputs error factor information to the information processing apparatus. Examples of the error factor information include the distance between an ultrasonic probe and a position and posture sensor. In general, the longer the distance, the larger the error caused by the projection (e.g., coordinate transformation).

Then, in step S2, a tomographic image acquisition unit acquires a tomographic image (e.g., ultrasonic tomographic image).

In step S3, the error acquisition unit acquires an error (an error caused by the projection described above). For example, if the error factor information acquired in step S1 is the distance between an ultrasonic probe and a position and posture sensor, an error may be determined using the distance by using a table (hereinafter referred to as "information for calculating an error") stored in advance.

In step S4, a range where a region of interest (lesion of interest) may exist (an error range caused by the projection described above, search range) is acquired. Specifically, an error range that includes a projected region obtained by projecting a given region in a three-dimensional image onto a plane including an ultrasonic tomographic image and that is caused by the projection described above is acquired. In this case, for example, a circle centered on the projected region and having a radius equal to the distance determined as an error is drawn, and a region where the circle overlaps the ultrasonic tomographic image is acquired.

Figure 5A:
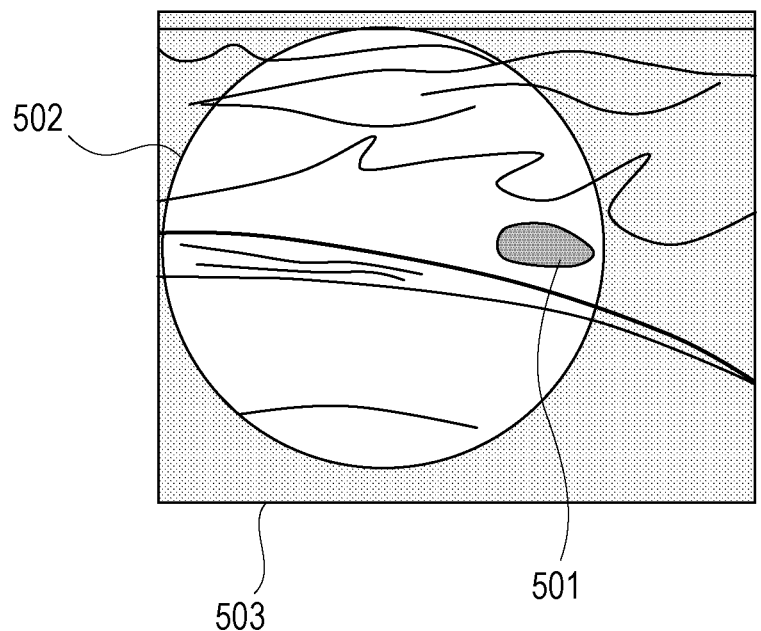
FIG. 5A is a diagram illustrating a method for displaying a tomographic image and an existence range in the information processing apparatus according to the first embodiment.

In step S5, the overlapping region is displayed on top of the ultrasonic tomographic image on a display unit. For example, an image illustrated in FIG. 5A is displayed on the display unit. In this case, a range (existence range) 502 where a corresponding lesion 501 may exist may be represented by a circle, a semi-transparent mask may be applied so as to surround the circle, and an ultrasonic tomographic image in an area inside the circle may be displayed in a normal manner. Thus, a search region within which the actual corresponding region of the region of interest is searched for can be clearly identified. In addition, the user can easily search for the actual corresponding region, and an efficient search can be achieved. A range where the corresponding region may exist may also be drawn with only a line of a circle. An area inside the range where the corresponding region may exist may be colored. In this case, the area may be transparent enough to search.

In FIG. 5A, the user can specify, as the position of the corresponding region, a given position in the error range caused by the projection on the ultrasonic tomographic image. For example, a mark (e.g., circle or cross) indicating the corresponding region (corresponding region of the given region in the two-dimensional image) can be displayed on the display unit in such a manner that the mark is overlaid on top of the given position on the two-dimensional image. This allows the position of the corresponding region in the two-dimensional image to be easily identified, resulting in an improvement in diagnosis efficiency. Furthermore, the error caused by the projection in the two-dimensional image may be corrected on the basis of the difference between the specified given position and the projected region. Therefore, the mark can be continuously displayed at the position corresponding to the given position in a two-dimensional image acquired again.

Figure 5B:
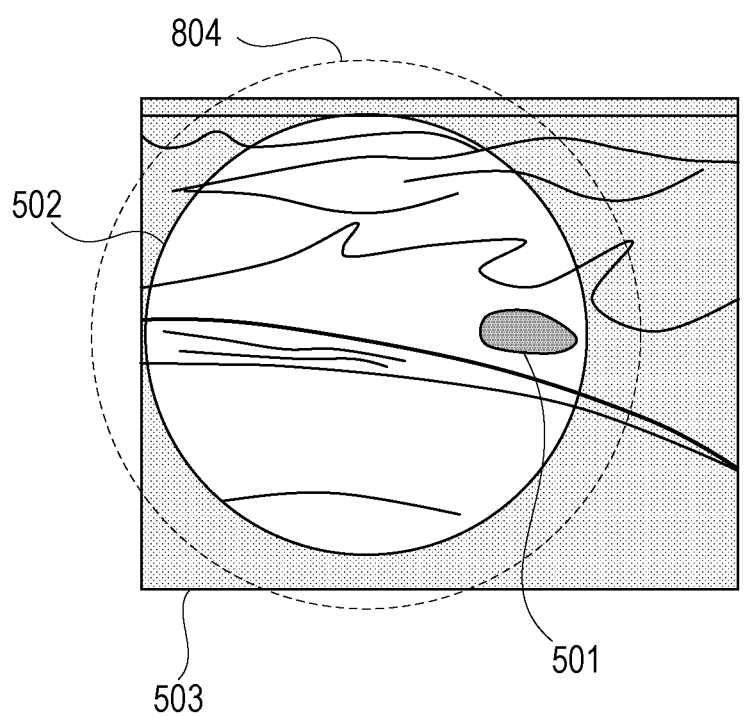
FIG. 5B is a diagram illustrating a method for displaying a tomographic image and an existence range in the information processing apparatus according to the second embodiment.

In FIG. 5A, if the user does not specify a given position, the acquisition of ultrasonic tomographic images is repeated. The size of the error range caused by the projection changes in accordance with the position and posture of each ultrasonic tomographic image. The size of the error range caused by the projection becomes maximum when the given region (first region) and the projected region (corresponding region of the first region in the ultrasonic tomographic image) are at the same position (when a scanned portion of the ultrasonic tomographic image passes the given region). As illustrated in FIG. 5B, an error range 804 having the maximum size may be displayed on top of an ultrasonic image 503 all the time so as to make the error range 804 distinguishable from the actual error range 502.

Second Embodiment

An information processing system according to a second embodiment is configured to display a region where a region of interest (e.g., a lesion of interest) in three-dimensional image data may exist in an ultrasonic tomographic image captured in real time. This enables an operator (such as a doctor or an engineer) to easily draw a corresponding region (corresponding lesion) that corresponds to the region of interest in the three-dimensional image data onto the ultrasonic tomographic image. In this embodiment, a description will be given of a case where a group of tomographic images representing three-dimensional information about the inside of the object is handled as the three-dimensional image data. The information processing system according to this embodiment will now be described.

Figure 2:
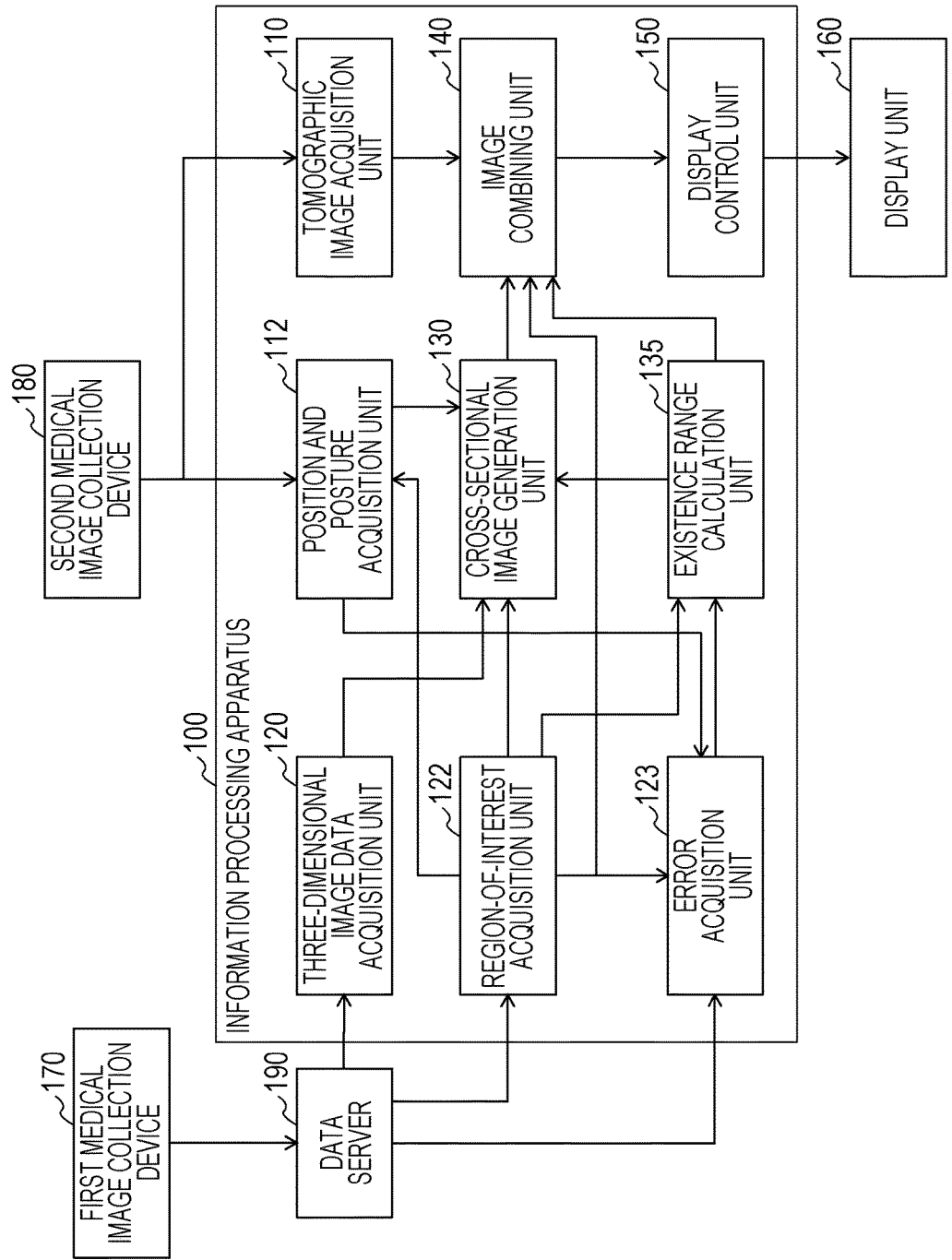
FIG. 2 is a block diagram illustrating a configuration of an information processing apparatus according to a second embodiment.

FIG. 2 illustrates the configuration of the information processing system according to this embodiment. As illustrated in FIG. 2, an information processing apparatus 100 according to this embodiment includes a tomographic image acquisition unit (also referred to as a "two-dimensional image acquisition unit") 110, a position and posture acquisition unit 112, a three-dimensional image data acquisition unit (also referred to as a "three-dimensional image acquisition unit") 120, a region-of-interest acquisition unit 122, an error acquisition unit 123, a cross-sectional image generation unit (also referred to as a "cross-sectional image acquisition unit") 130, an existence range calculation unit 135, an image combining unit 140, and a display control unit 150. The information processing apparatus 100 is connected to a data server 190 that holds three-dimensional image data, error factor information described below, and any other suitable data. The information processing apparatus 100 is also connected to an ultrasonic diagnostic imaging apparatus serving as a second medical image collection device 180 used to capture an ultrasonic tomographic image of an object.

[Input of Three-Dimensional Image Data]

The three-dimensional image data held in the data server 190 represents a group of reference tomographic images obtained by capturing images of an object in advance using a first medical image collection device 170 such as an MRI apparatus or an X-ray CT apparatus. In the following description, byway of example, an MRI apparatus is used as the first medical image collection device 170, and the human breast is used as the object for which images are to be captured.

A group of reference tomographic images captured by an MRI apparatus is represented by three-dimensional image data, and the position and posture of each tomographic image are represented as a position and posture in the MRI apparatus coordinate system. The term "MRI apparatus coordinate system", as used herein, refers to a coordinate system whose origin is defined as one point in a space with respect to the MRI apparatus. The three-dimensional image data represented using the MRI apparatus coordinate system is acquired by the three-dimensional image data acquisition unit 120, and is input to the information processing apparatus 100. The three-dimensional image data acquisition unit 120 generates three-dimensional volume data with each three-dimensional voxel representing a luminance value, from the group of reference tomographic images, and holds the generated three-dimensional volume data. The three-dimensional image data acquisition unit 120 outputs the held three-dimensional volume data to the cross-sectional image generation unit 130 in response to a request from the cross-sectional image generation unit 130.

The data server 190 further holds the position of a prespecified lesion (lesion of interest) as a region of interest in the three-dimensional image data. The position of the lesion of interest can be specified by, for example, sequentially displaying a group of reference tomographic images on an image viewer (not illustrated), prompting the operator to select one of the reference tomographic images in which the lesion of interest appears, and clicking a mouse (not illustrated) on the lesion of interest. The position of the lesion of interest held in the data server 190 is acquired by the region-of-interest acquisition unit 122, and is input to the information processing apparatus 100. The region-of-interest acquisition unit 122 also outputs the held position of the lesion of interest to the error acquisition unit 123, the existence range calculation unit 135, and the image combining unit 140. In the following description, like the three-dimensional image data, the position of the lesion of interest is also represented using the MRI apparatus coordinate system.

[Acquisition of Estimated Error Value: Second Embodiment]

The data server 190 further holds information for calculating an error in the position of the lesion in the three-dimensional image data. The information for calculating an error is information for calculating the degree of error involved in the position of the corresponding region (corresponding lesion) in the ultrasonic tomographic image which corresponds to the lesion of interest in the three-dimensional image data during the projection. In other words, the information for calculating an error is information for calculating an error in position alignment (existence range of the corresponding lesion) between the three-dimensional image data and the ultrasonic tomographic image. In this embodiment, the position and posture acquisition unit 112 calculates a position and posture of an ultrasonic tomographic image in the MRI apparatus coordinate system, thereby achieving position alignment between the three-dimensional image data and the ultrasonic tomographic image. In the following description, the information for calculating an estimated error value is referred to as "error factor information" (which will be described in detail below). The error factor information held in the data server 190 is input to the information processing apparatus 100 via the error acquisition unit 123. The error acquisition unit 123 calculates an estimated error value in position alignment (existence range of the corresponding lesion) between the three-dimensional image data and the ultrasonic tomographic image in accordance with the error factor information. The error acquisition unit 123 outputs the calculated estimated error value to the existence range calculation unit 135. In this case, the existence range calculation unit 135 calculates a circle obtained by cutting a sphere centered on the position of the lesion of interest and having a radius equal to an error along an ultrasonic cross section, and outputs the calculated circle to the image combining unit 140 as information indicating the existence range of the corresponding lesion.

[Acquisition of Tomographic Image: Second Embodiment]

The ultrasonic diagnostic imaging apparatus serving as the second medical image collection device 180 captures ultrasonic tomographic images of an object in real time. The ultrasonic tomographic images are acquired by the tomographic image acquisition unit 110, and are sequentially input to the information processing apparatus 100. The tomographic image acquisition unit 110 further converts the acquired ultrasonic tomographic images into digital data, if necessary, and holds the ultrasonic tomographic images in association with the position and posture acquired from the position and posture acquisition unit 112. The tomographic image acquisition unit 110 outputs an ultrasonic tomographic image held therein to the image combining unit 140 in response to a request from the image combining unit 140.

Generally, an operator captures images of an object with an ultrasonic probe held by hand while moving the ultrasonic probe as desired. The ultrasonic probe serves as an imaging unit (not illustrated) in the ultrasonic diagnostic imaging apparatus. Using the ultrasonic probe, an ultrasonic wave can be detected and an ultrasonic tomographic image can be acquired. In this case, the ultrasonic tomographic image does not clearly represent a position and posture captured in a space with respect to the object. In this embodiment, therefore, the position and posture of the ultrasonic probe are measured using a position and posture sensor (not illustrated) attached to the ultrasonic diagnostic imaging apparatus. The position and posture sensor may be, for example, a FASTRAK (registered trademark) sensor, developed by Polhemus Incorporated, Colchester, USA. Any type of position and posture sensor capable of measuring the position and posture of the ultrasonic probe may be used.

The position and posture of the ultrasonic probe obtained in the above manner are acquired by the position and posture acquisition unit 112, and are input to the information processing apparatus 100. The position and posture of the ultrasonic probe may be represented as, for example, the position and posture in the reference coordinate system. The term "reference coordinate system", as used herein, refers to a coordinate system whose origin is defined as one point in a space with respect to the object. Further, the position and posture acquisition unit 112 acquires the position and posture of the ultrasonic probe in the reference coordinate system, and calculates the position and posture of the ultrasonic tomographic image in the MRI apparatus coordinate system in accordance with the acquired position and posture. The position and posture acquisition unit 112 outputs the calculated position and posture to the cross-sectional image generation unit 130 in response to a request from the cross-sectional image generation unit 130. This calculation process is based on a relative positional relationship between the ultrasonic probe and the ultrasonic tomographic image and based on a relative positional relationship between the reference coordinate system and the MRI apparatus coordinate system by using a known coordinate transformation computation. In this embodiment, information about the above relative positional relationships (hereinafter, calibration data) is derived in advance using a known calibration method, and is held as known values in a memory in the position and posture acquisition unit 112.

[Generation of Cross-Sectional Image: Second Embodiment]

The cross-sectional image generation unit 130 receives the three-dimensional volume data output from the three-dimensional image data acquisition unit 120, the position and posture of the ultrasonic tomographic image output from the position and posture acquisition unit 112, and the position of the lesion of interest output from the region-of-interest acquisition unit 122. The cross-sectional image generation unit 130 generates a cross-sectional image (second two-dimensional cross-sectional image) from the three-dimensional volume data on the basis of the received pieces of data, and outputs the cross-sectional image to the image combining unit 140. The cross-sectional image generation unit 130 performs different processes in accordance with two operation modes described below. The image combining unit 140 acquires information indicating an existence range of a corresponding lesion (second region) from the existence range calculation unit 135, and draws the second region on top of the ultrasonic tomographic image acquired from the tomographic image acquisition unit 110. The image combining unit 140 further combines the resulting image with the cross-sectional image acquired from the cross-sectional image generation unit 130 to generate a composite image, and outputs the composite image to the display control unit 150 or to an external device. An image in which the existence range of the corresponding lesion is overlaid on top of the ultrasonic tomographic image and an image in which the given region (first region) is overlaid on top of the cross-sectional image may be displayed side-by-side on a display unit. The display control unit 150 acquires the composite image output from the image combining unit 140, and causes the composite image to be displayed on a display unit 160.

At least some of the units illustrated in FIG. 2 (i.e., the tomographic image acquisition unit 110, the position and posture acquisition unit 112, the three-dimensional image data acquisition unit 120, the region-of-interest acquisition unit 122, the error acquisition unit 123, the cross-sectional image generation unit 130, the existence range calculation unit 135, the image combining unit 140, and the display control unit 150) may be implemented as independent devices. Alternatively, each of the individual units may be implemented by software for implementing the functions thereof by installing the unit into one or a plurality of computers and executing the software using a central processing unit (CPU) in the computer. In this embodiment, it is assumed that the individual units are implemented by software, and are installed into a single computer.

[Basic Configuration of Computer: Second Embodiment]

Figure 17:
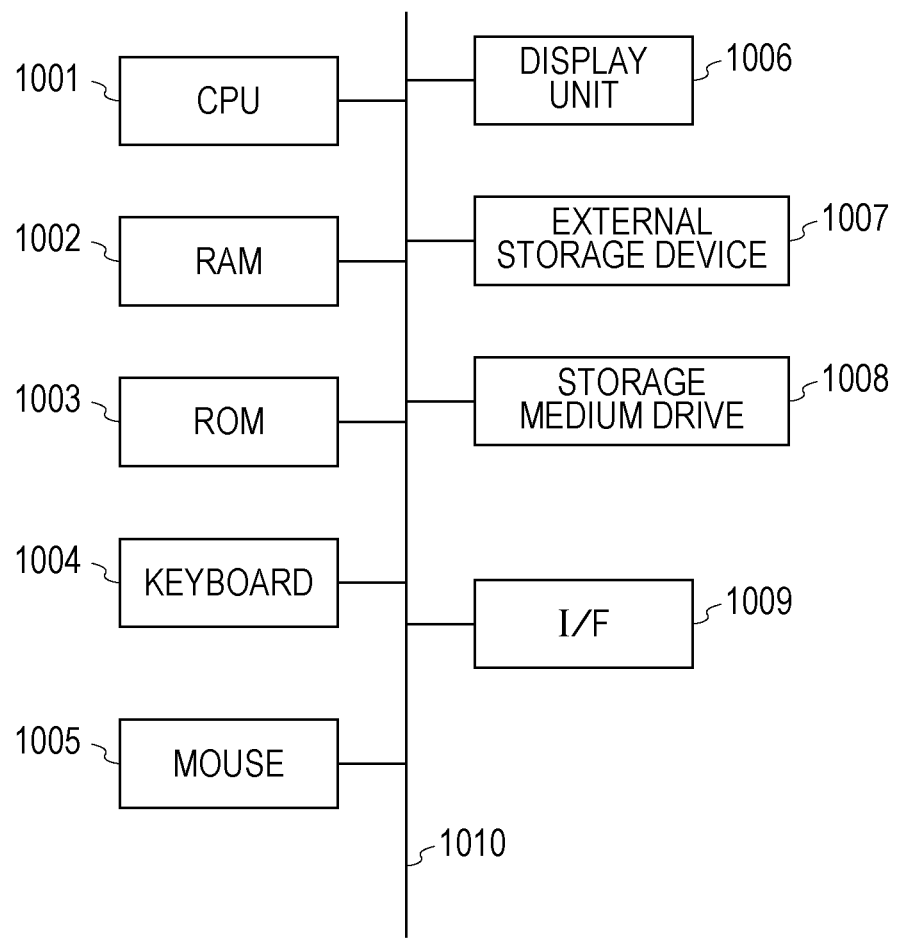
FIG. 17 is a diagram illustrating a basic configuration of a computer capable of implementing individual units of an information processing apparatus according to an embodiment by software.

FIG. 17 is a diagram illustrating the basic configuration of a computer that executes software to implement the functions of each of the tomographic image acquisition unit 110, the position and posture acquisition unit 112, the three-dimensional image data acquisition unit 120, the region-of-interest acquisition unit 122, the error acquisition unit 123, the cross-sectional image generation unit 130, the existence range calculation unit 135, the image combining unit 140, and the display control unit 150.

A CPU 1001 controls the overall operation of the computer using a program and data stored in a random access memory (RAM) 1002 or a read-only memory (ROM) 1003. The CPU 1001 further controls the execution of software to implement the functions of each of the tomographic image acquisition unit 110, the position and posture acquisition unit 112, the three-dimensional image data acquisition unit 120, the region-of-interest acquisition unit 122, the error acquisition unit 123, the cross-sectional image generation unit 130, the existence range calculation unit 135, the image combining unit 140, and the display control unit 150.

The RAM 1002 has an area for temporarily storing a program and data loaded from an external storage device 1007 or a storage medium drive 1008, and also has a work area used when the CPU 1001 performs various processes.

The ROM 1003 generally stores programs, setting data, etc. of the computer. A keyboard 1004 and a mouse 1005 are input devices, and the operator can input various instructions to the CPU 1001 using the keyboard 1004 and the mouse 1005.

A display unit 1006 may be formed of a cathode-ray tube (CRT) display, a liquid crystal display, or any other suitable display, and corresponds to the display unit 160. The display unit 1006 can display the items to be displayed for image processing, such as a message and a graphical user interface (GUI), as well as the composite image generated by the image combining unit 140.

The external storage device 1007 is a device functioning as a large-capacity information storage device such as a hard disk drive, and stores an operating system (OS), a program to be executed by the CPU 1001, and the like. In this embodiment, the "known information" is stored in the external storage device 1007, and is loaded into the RAM 1002 as necessary.

The storage medium drive 1008 reads a program and data stored in a storage medium such as a compact disk ROM (CD-ROM) or a digital versatile disc ROM (DVD-ROM) in accordance with an instruction from the CPU 1001, and outputs the read program and data to the RAM 1002 and the external storage device 1007.

An interface (I/F) 1009 includes an analog video port or a digital input/output port such as an Institute of Electrical and Electronics Engineers (IEEE) 1394 port, and an Ethernet (registered trademark) port through which information such as the composite image is output to outside. Data input to each port is captured into the RAM 1002 via the I/F 1009. Some of the functions of the tomographic image acquisition unit 110, the position and posture acquisition unit 112, the three-dimensional image data acquisition unit 120, the region-of-interest acquisition unit 122, and the error acquisition unit 123 are implemented by the I/F 1009.

The structural elements described above are connected to one another via a bus 1010.

[Search Mode and Linked Operation Mode]

The information processing system described above has two operation modes, a search mode (mode for searching for the corresponding lesion) and a linked operation mode (mode for observing and checking associated lesions). When a position and posture of the ultrasonic tomographic image and the position of the lesion of interest are given, a cross-sectional image is generated (or acquired) in accordance with the current mode from the MRI three-dimensional image data on the basis of the above pieces of information. The cross-sectional image generated in the search mode is a cross-sectional image that is parallel to a plane including the ultrasonic tomographic image described above and that passes the lesion of interest. By generating a cross-sectional image in the above manner, it is possible to display the inclinations (postures) of the ultrasonic probe with respect to the object in two cross-sectional images (ultrasonic tomographic image and MRI cross-sectional image) in an aligned manner all the time regardless of the posture of the ultrasonic probe. Consequently, the operator may only be required to match the position against which the ultrasonic probe is pressed to that in the MRI data. Since a time-consuming and laborious operation for aligning the inclinations with each other is no longer necessary, the operator can easily achieve position alignment. The switching between the search mode and the linked operation mode is performed by specifying the corresponding lesion in the ultrasonic tomographic image and pointing out the position of the corresponding lesion. In the linked operation mode, an image obtained by cutting the same cross section as that of the ultrasonic tomographic image from the MRI three-dimensional image data is displayed as an MRI cross-sectional image. In the linked operation mode, the operator is able to observe the spread of the lesion, etc., while simultaneously viewing the ultrasonic tomographic image and the MRI cross-sectional image of the surroundings of the lesion of interest which are linked to the position and posture of the ultrasonic probe.

The ultrasonic tomographic image and the MRI cross-sectional image are displayed on the display unit 160. In the search mode, the operator is able to perform position alignment by comparing the features appearing in the respective images to determine whether or not both match while changing the position against which the ultrasonic probe is pressed. In the linked operation mode, the operator is able to observe the surroundings of the lesion while viewing the respective images which have been aligned in position.

Figure 3:
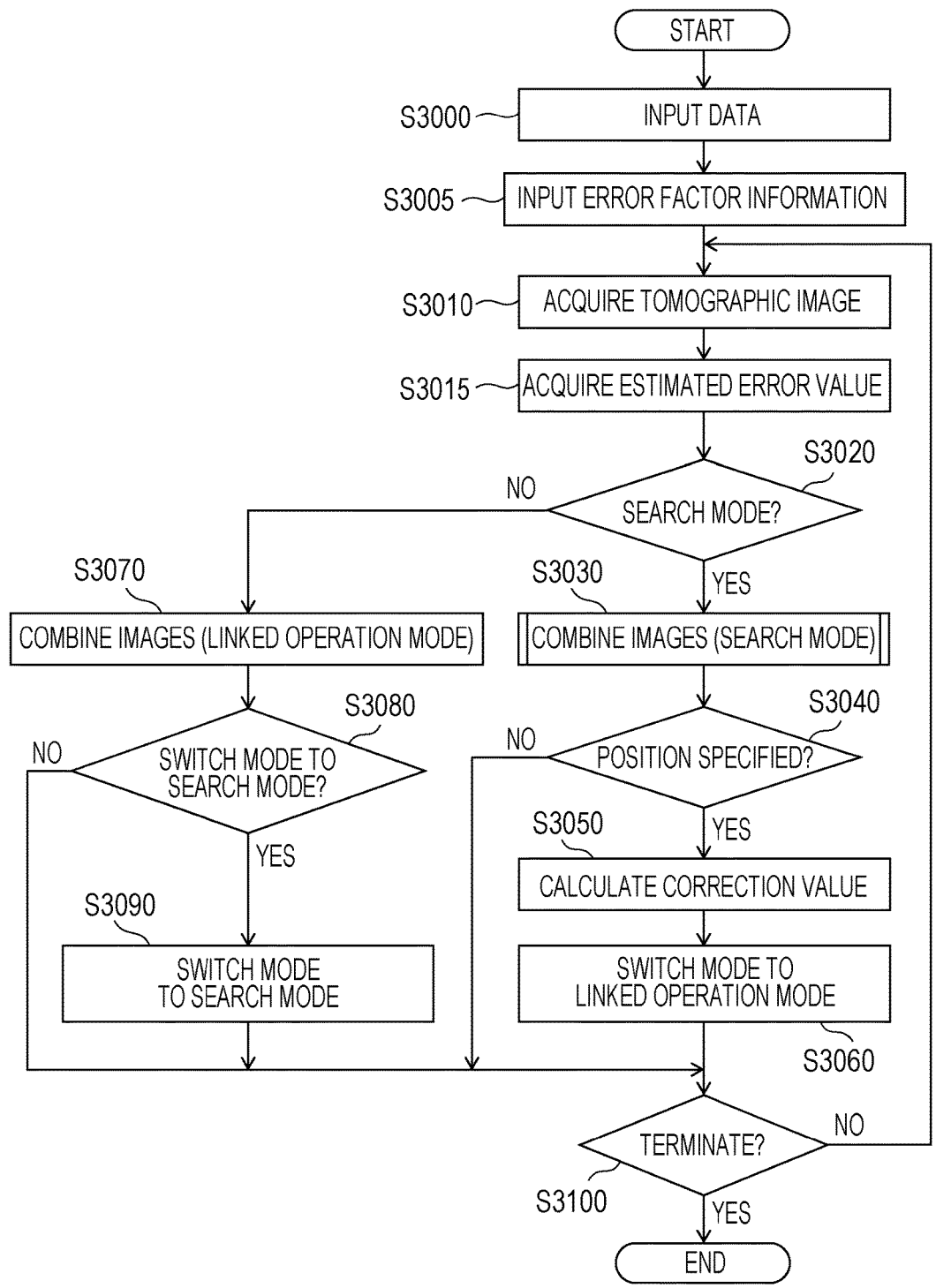
FIG. 3 is a flow diagram illustrating a processing procedure of the information processing apparatus according to the second embodiment.

FIG. 3 is a flowchart illustrating a processing procedure of the information processing apparatus 100. In this embodiment, the procedure in the flowchart is implemented by executing a program implementing the functions of the individual units by the CPU 1001. Before the following process is performed, a program code based on the flowchart has been loaded from, for example, the external storage device 1007 into the RAM 1002.

[S3000: Input of Data]

In step S3000, as a process of the three-dimensional image data acquisition unit 120, the information processing apparatus 100 acquires a group of reference tomographic images as three-dimensional image data from the data server 190. Then, the information processing apparatus 100 generates three-dimensional volume data with each three-dimensional voxel representing a luminance value, from the group of reference tomographic images through three-dimensional arrangement and interpolation of the pixels of each of the tomographic images. Further, as a process of the region-of-interest acquisition unit 122, the information processing apparatus 100 acquires the position of the lesion of interest from the data server 190.

[S3005: Input of Error Factor Information]

In step S3005, as a process of the error acquisition unit 123, the information processing apparatus 100 acquires from the data server 190 various kinds of error factor information (described below) to be used to calculate an estimated error value.

[S3010: Acquisition of Tomographic Image]

In step S3010, as a process of the tomographic image acquisition unit 110, the information processing apparatus 100 acquires an ultrasonic tomographic image from the second medical image collection device 180. Further, as a process of the position and posture acquisition unit 112, the information processing apparatus 100 acquires from the second medical image collection device 180 the position and posture of the ultrasonic probe obtained when the ultrasonic tomographic image is obtained. The information processing apparatus 100 then calculates the position and posture of the ultrasonic tomographic image in the MRI apparatus coordinate system, from the position and posture of the ultrasonic probe in the reference coordinate system by using the calibration data described above, which is stored in advance as a known value. If a correction parameter for position alignment is held, the information processing apparatus 100 corrects the calculated position value of the ultrasonic tomographic image by an amount corresponding to the correction parameter to accurately align the lesion of interest with the corresponding lesion. A relative relationship between the lesion of interest (region of interest) and the tomographic image is estimated by the acquisition of the position of the lesion of interest in step S3000 and the calculation of the position and posture of the ultrasonic tomographic image in step S3010.

[S3015: Acquisition of Estimated Error Value]

In step S3015, as a process of the error acquisition unit 123, the information processing apparatus 100 calculates an estimated error value on the basis of the various kinds of data used to calculate an error, which is acquired in step S3005.

In this embodiment, a relationship between the MRI apparatus coordinate system and the reference coordinate system is represented by a rigid-body transformation. However, an exact rigid-body transformation may not necessarily be provided between the position and posture of the object in the MRI apparatus coordinate system obtained when an MRI image is captured and the position and posture of the object in the reference coordinate system obtained when ultrasonic imaging is performed. Therefore, an error may exist when the relationship between the coordinate systems is represented by a rigid-body transformation. If a difference in position and posture of an object between the coordinate systems provides an exact rigid-body transformation, it is actually difficult to correctly determine the rigid-body transformation, and an error may exist. The error which may exist also includes an error in measured position and posture values acquired by the position and posture acquisition unit 112 (position and posture measurement error).

A process of calculating an estimated error value can be executed based on, for example, the characteristics of a position and posture sensor configured to measure the position and posture of the ultrasonic probe of the second medical image collection device 180. For example, a reference error value may be determined in advance for each measurement method of the position and posture sensor, and a value may be selected in accordance with the measurement method of the sensor to be used. For example, magnetic sensors generally have lower measurement accuracy than optical sensors. Thus, a smaller estimated error value can be calculated than an estimated error value calculated when information indicating that an optical sensor is in use is acquired as error factor information from the data server 190 and when a magnetic sensor is used in accordance with the acquired information. In addition, an estimated error value can be calculated, regardless of the difference between the measurement methods of position and posture sensors, in accordance with a relationship of the spatial position and posture to a measurement standard of the position and posture sensor. For example, when the position and posture sensor is a magnetic sensor, an estimated error value can be defined as a function of the distance between the magnetic generator, or a measurement standard, and the ultrasonic probe, and a large value can be calculated as an estimated error value when the distance is large. Also, when the position and posture sensor is an optical sensor, an estimated error value can be calculated in accordance with the distance between the measurement standard and the ultrasonic probe, the posture of the ultrasonic probe, etc.

An estimated error value can also be calculated on the basis of a portion or the like of the object where the lesion of interest exists. For example, when the lesion of interest exists in the soft tissue of the breast or the like of the object, it is anticipated that this portion of the object may deform during a period between the capture time of the MRI image and the capture time of the ultrasonic image. Therefore, when the lesion of interest exists in the above portion, a large estimated error value can be calculated. Also, a large estimated error value can be calculated for the region of the heart and a region near the heart where a position varies largely due to heart beats or the region of the lung and a region near the lung where a position varies largely due to breathing. Specifically, information indicating a portion (the name of an organ or a position in an organ) in the object where the lesion of interest exists, and data (table) showing a correspondence between the portion and the magnitude of an error can be acquired as error factor information, and an estimated error value can be calculated on the basis of the above pieces of information.

In addition, information about the position or the like of portions used as indices for calibration between the MRI apparatus coordinate system and the reference coordinate system can be acquired as error factor information, and an estimated error value can be calculated on the basis of relationships between these portions and the position of the lesion of interest. For example, if the xiphoid process of the object is used as an index used for calibration, an estimated error value can be calculated as a function of the distance between the position of the xiphoid process in the MRI image and the lesion of interest. Also, if the position of the papilla is used as an index used for calibration, an estimated error value can be calculated as a function of the distance between the position of the papilla in the MRI image and the lesion of interest. Alternatively, an estimated error value may be acquired by estimating errors in a complex manner using a plurality of methods among the methods described above by way of example.

[S3020: Determination of Search Mode]

In step S3020, the information processing apparatus 100 determines whether the current operation mode is the search mode or the linked operation mode. If the operation mode is the search mode, the process proceeds to step S3030; if the operation mode is the linked operation mode, the process proceeds to step S3070. In this embodiment, it is assumed that the initial operation mode is the search mode.

[S3030: Generation and Display of Image in Search Mode]

In step S3030, the information processing apparatus 100 generates an image in the search mode, and displays the generated image. The details of the processing of step S3030 will be described below with reference to a flowchart illustrated in FIG. 4.

When the operator specifies the position of the corresponding lesion in the ultrasonic tomographic image, the information processing apparatus 100 performs the following processing (steps S3040 and S3050) to correct the misalignment between the position of the lesion of interest and the position at which the corresponding lesion actually exists.

[S3040: Specification of Position of Corresponding Lesion in Tomographic Image]

In step S3040, as a process of the position and posture acquisition unit 112, the information processing apparatus 100 determines whether or not the position of the corresponding lesion in the ultrasonic tomographic image has been specified. The position of the corresponding lesion may be specified by the operator by, for example, clicking the mouse 1005 on the position of the corresponding lesion in the ultrasonic tomographic image displayed on the display unit 160. If the position of the corresponding lesion has been specified, the information processing apparatus 100 calculates the position of the corresponding lesion in the MRI apparatus coordinate system in accordance with the position of the corresponding lesion in the ultrasonic tomographic image and in accordance with the position and posture of the ultrasonic tomographic image. Then, the process proceeds to step S3050. If no positions have been specified, the process proceeds to step S3100. For example, if the corresponding lesion is not displayed in the ultrasonic tomographic image, in step S3010, the user acquires an ultrasonic tomographic image again without specifying a position.

[S3050: Calculation of Correction Value]

In step S3050, as a process of the position and posture acquisition unit 112, the information processing apparatus 100 calculates an offset (correction value) between the position of the corresponding lesion acquired in step S3040 and the position of the lesion of interest acquired in step S3000. Then, the obtained value is held in the memory as a correction parameter for position alignment. If a correction parameter is held, the position and posture acquisition unit 112 converts the ultrasonic tomographic image newly acquired in S3010 into that of the MRI apparatus coordinate system, and corrects (or subtracts) the position of the ultrasonic tomographic image in the obtained coordinate system by an amount corresponding to the correction parameter (offset). Therefore, the influence of a measurement error of the position and posture sensor, the deformation of the object, etc., can be corrected.

[S3060: Switching from Search Mode to Linked Operation Mode]

In step S3060, the information processing apparatus 100 switches the operation mode of the system from the search mode to the linked operation mode, and the process proceeds to step S3100. In the linked operation mode, it is possible to continuously acquire ultrasonic tomographic images corrected in the manner described above without performing the step of specifying positions from the ultrasonic tomographic images. For example, the user may wish to observe the spread of the lesion in order to obtain the size of the lesion to be removed surgically. In this case, it is possible to observe the surroundings of the corresponding lesion using the corrected ultrasonic tomographic images.

[S3070: Generation and Display of Image in Linked Operation Mode]

In step S3070, the information processing apparatus 100 generates an image in the linked operation mode, and displays the generated image. Specifically, as a process of the cross-sectional image generation unit 130, the information processing apparatus 100 generates a cross-sectional image obtained by cutting the same cross section as that of the ultrasonic tomographic image obtained in step S3010 from the three-dimensional volume data, in accordance with the position and posture of the tomographic image. Then, as a process of the image combining unit 140, the information processing apparatus 100 combines the ultrasonic tomographic image obtained in step S3010 with the cross-sectional image obtained in step S3070. For example, an image in which the above images are horizontally arranged side by side may be generated. If the position of the lesion of interest exists in the plane of the cross-sectional image, rectangular marks or the like indicating the lesion of interest may be drawn at the corresponding positions in the ultrasonic tomographic image and the cross-sectional image so that the rectangular marks or the like are superimposed on the respective images. Further, as a process of the display control unit 150, the information processing apparatus 100 displays the composite image on the display unit 160.

[S3080: Determination of Switching from Linked Operation Mode to Search Mode]

In step S3080, the information processing apparatus 100 determines whether or not to switch the operation mode of the system from the linked operation mode to the search mode. For example, a switching instruction input by, for example, pressing a predetermined key (operation mode switching key) on the keyboard 1004 by the operator is acquired. If it is determined that the operation mode is to be switched, the process proceeds to step S3090; if it is determined that the operation mode is not to be switched, the process proceeds to step S3100. For example, when an image similar to an image of the corresponding lesion is being displayed, it is probable that the user has specified a region different from the region of the actual corresponding lesion in S3040. In this case, the user can observe the surroundings of the corresponding lesion using the ultrasonic tomographic image acquired again in the linked operation mode. When the user finds the actual corresponding lesion, the user can switch the operation mode to the search mode in step S3080, and can acquire the position of the corresponding lesion again.

[S3090: Switching from Linked Operation Mode to Search Mode]

In step S3090, the information processing apparatus 100 switches the operation mode of the system from the linked operation mode to the search mode, and the process proceeds to step S3100.

[S3100: Determination of Termination of Whole Process]

In step S3100, the information processing apparatus 100 determines whether or not to terminate the whole process. For example, a termination instruction input by, for example, pressing a predetermined key (end key) on the keyboard 1004 by the operator is acquired. If it is determined that the process is to be terminated, the whole process of the information processing apparatus 100 ends. If it is determined that the process is not to be terminated, the process returns to step S3010, and the processing of step S3010 and subsequent steps is executed again on a new captured ultrasonic tomographic image.

Accordingly, the process of the information processing apparatus 100 is executed.

[Generation and Display of Image in Search Mode]

Next, the details of a process for generating an image to be displayed in the search mode in the information processing apparatus 100 in step S3030, will be described with reference to a flowchart in FIG. 4.

[S4000: Acquisition of Cross-Sectional Image]

In step S4000, as a process of the cross-sectional image generation unit 130, the information processing apparatus 100 generates a cross-sectional image in the search mode in accordance with the three-dimensional volume data and the position of the lesion of interest obtained in step S3000 and in accordance with the position and posture of the ultrasonic tomographic image obtained in step S3010.

First, the cross-sectional image generation unit 130 calculates a cross section (plane) based on the position of the lesion of interest and the posture of the ultrasonic tomographic image. Specifically, first, the position and posture of the cross section coordinate system (coordinate system indicating the position and posture of the cross section) are initialized. Then, the cross section is rotated so that the posture of the cross section matches the posture of the ultrasonic tomographic image. Then, the cross section is translated so that the lesion of interest is located on top of the cross section. The cross section calculated accordingly is a cross section that includes the lesion of interest (that is, a plane representing the cross section passes the lesion of interest) and that has the same posture as that of the ultrasonic tomographic image (parallel to the ultrasonic tomographic image). Finally, a range in which a cross-sectional image is to be generated on the cross section is calculated. For example, the positions of points at the four corners of the ultrasonic tomographic image are calculated on the basis of the position and posture of the ultrasonic tomographic image, and a range of a cross-sectional image to be generated is determined using four points composed of the feet of the perpendicular lines to the cross section from the respective points. Therefore, as the posture of the ultrasonic tomographic image is moved, the posture of the cross-sectional image is also moved accordingly, thus allowing the user to achieve easy observation.

Finally, the cross-sectional image generation unit 130 generates the image corresponding to the cross section determined in the above manner by cutting the image from the three-dimensional volume data. A method for generating an image of a specified cross section by cutting the image from three-dimensional volume data is known, and the detailed description thereof is thus omitted.

[S4010: Acquisition of Existence Range of Lesion of Interest]

In step S4010, as a process of the existence range calculation unit 135, the information processing apparatus 100 calculates the existence range of the corresponding lesion in the ultrasonic tomographic image obtained in step S3010. In this embodiment, an existence range of a corresponding lesion in the three-dimensional space is defined as a sphere centered on the position of the lesion of interest obtained in step S3000 and having a radius equal to the estimated error value obtained in step S3015. Further, the existence range of the corresponding lesion in the ultrasonic tomographic image is defined as a circle that is a region (cross section of the sphere) where the sphere representing the existence range of the corresponding lesion in the three-dimensional space and the tomographic image intersect. Therefore, the image combining unit 140 calculates the center position and the radius of the circle in the ultrasonic tomographic image. A method for calculating a region where a sphere defined in the three-dimensional space and a plane intersect is known, and the description thereof is thus omitted. If a sphere representing an existence range and an ultrasonic tomographic image do not intersect, information indicating "no existence ranges in the cross section" is stored.

[S4020: Drawing of Existence Range of Lesion of Interest in Tomographic Image]

In step S4020, as a process of the image combining unit 140, the information processing apparatus 100 draws information indicating the existence range of the corresponding lesion in the ultrasonic tomographic image calculated in step S4010, on top of the ultrasonic tomographic image. In this case, a range where a corresponding lesion may exist may be represented by a circle, a semi-transparent mask may be applied so as to surround the circle, and an ultrasonic tomographic image in an area inside the circle may be displayed in a normal manner. Thus, a search region within which the actual corresponding lesion is searched for can be clearly identified. In addition, the user can easily search for the actual corresponding lesion, and an efficient search can be achieved. A range where the corresponding lesion may exist may also be drawn with only a line of a circle. An area inside the range where the corresponding region may exist may be colored. In this case, the area may be transparent enough to search. As a result of the processing of step S4020, the ultrasonic tomographic image 503 illustrated in FIG. 5A in which the existence range 502 of the corresponding lesion 501 is overlaid on top of the tomographic image is generated. It is to be noted that if "no existence ranges in the cross section" is determined in step S4010, the processing of step S4020 is not executed.

[S4030: Combining of Tomographic Image and Cross-Sectional Image]

In step S4030, as a process of the image combining unit 140, the information processing apparatus 100 combines the cross-sectional image obtained in step S4000 with the ultrasonic tomographic image obtained in step S4020 (specifically, an image in which an existence range of a corresponding lesion is overlaid on top of a tomographic image) to generate a composite image. For example, an image in which the above images are horizontally arranged side by side may be generated. Then, as a process of the display control unit 150, the information processing apparatus 100 displays the composite image on the display unit 160. The composite image is also output to an external device, if necessary, through the I/F 1009, and is also stored in the RAM 1002 so as to be available from another application.

Accordingly, a composite image in which a cross-sectional image having the same posture as an ultrasonic tomographic image and including the lesion of interest is combined with an ultrasonic tomographic image in which the existence range of the corresponding lesion is drawn is presented to the operator.

In the information processing apparatus according to this embodiment, therefore, an existence range of a corresponding lesion that takes an error in position alignment into account is presented on top of an ultrasonic tomographic image to help the operator search for the corresponding lesion. The presentation of the existence range of the corresponding lesion can reduce an undesired work of searching a range larger than necessary and can reduce the load on the operator during the search operation. Additionally, since the search range can be limited, the risk that the operator may perform erroneous association can be reduced.

In the embodiment described above, when an existence range of a corresponding lesion is presented on top of an ultrasonic tomographic image, a cross-sectional image having the same posture as the ultrasonic tomographic image and including the lesion of interest is presented as an MRI cross-sectional image. However, the MRI cross-sectional image to be presented may be in any other form. For example, similarly to the linked operation mode according to this embodiment, a cross-sectional image that is linked to both the position and posture of the ultrasonic tomographic image (obtained by cutting the same cross section as the ultrasonic tomographic image) may be displayed. In addition, an MRI cross-sectional image specified by a doctor may be displayed as a still image (without the linking of the posture). For example, an MRI cross-sectional image in which a doctor has pointed out the lesion of interest may be displayed. Furthermore, an MRI cross-sectional image may not necessarily be displayed.

Additionally, when a cross-sectional image that is linked to both the position and posture of the ultrasonic tomographic image are displayed, the number of lesions of interest may be plural. In this case, the existence range of the corresponding lesion in the three-dimensional space is defined as a sphere for each lesion of interest. Thus, a region where each sphere and the ultrasonic tomographic image intersect may be determined, and may be displayed as the existence range of the corresponding lesion in the tomographic image.

Third Embodiment

An information processing system according to a third embodiment is configured to display a region where a corresponding region (corresponding lesion) of a region of interest (e.g., a lesion of interest) in three-dimensional image data (reference image) may exist, in an ultrasonic tomographic image (target image) captured in real time. This enables an operator (such as a doctor or an engineer) to easily search for and identify the corresponding region in the ultrasonic tomographic image. The information processing system according to this embodiment will now be described.

Figure 7:
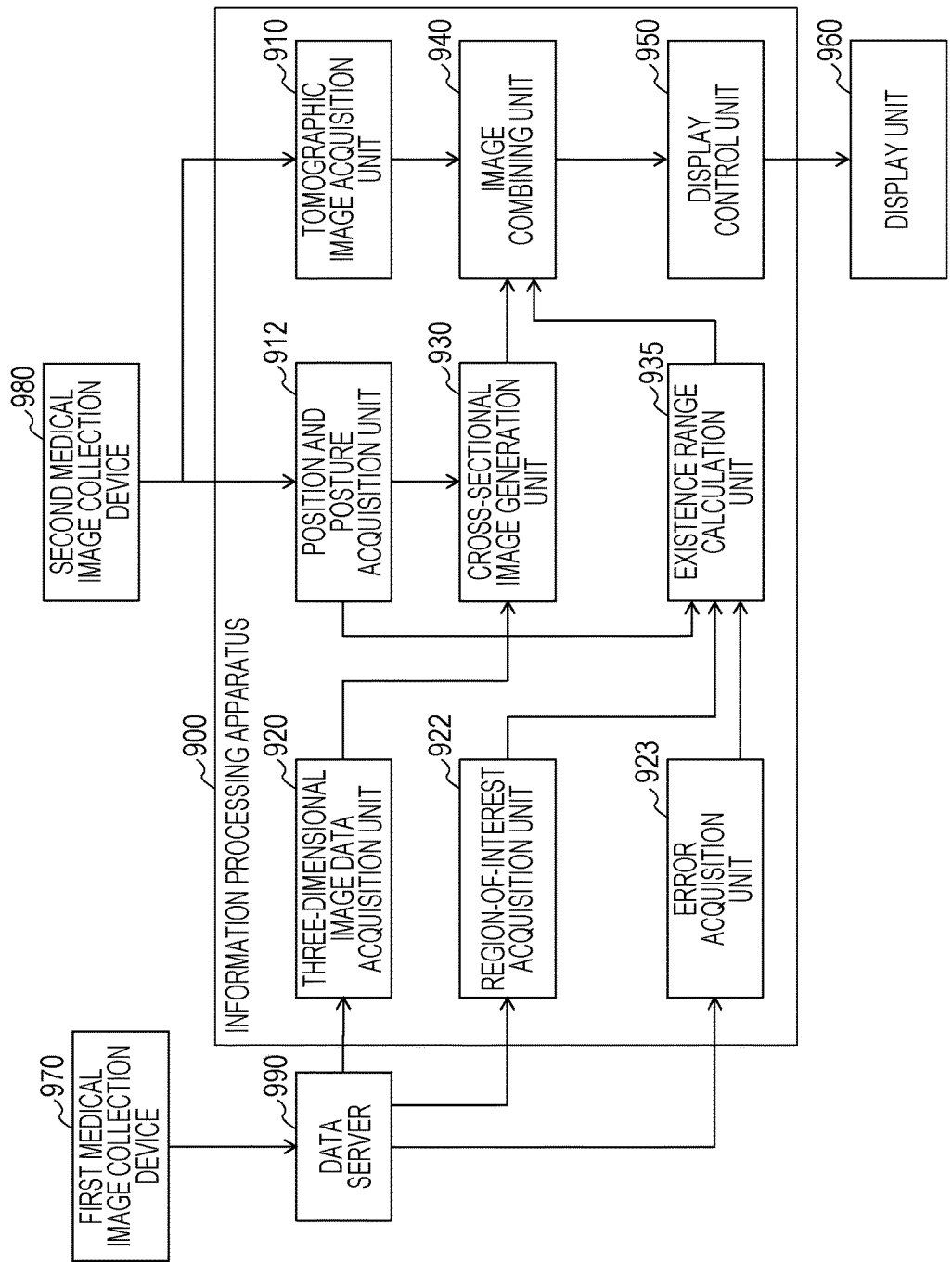
FIG. 7 is a diagram illustrating a device configuration of an information processing apparatus according to a third embodiment.

FIG. 7 illustrates the configuration of the information processing system according to this embodiment. As illustrated in FIG. 7, an information processing apparatus 900 according to this embodiment includes a tomographic image acquisition unit (also referred to as a "two-dimensional image acquisition unit") 910, a position and posture acquisition unit 912, a three-dimensional image data acquisition unit (also referred to as a "three-dimensional image acquisition unit") 920, a region-of-interest acquisition unit 922, an error acquisition unit 923, a cross-sectional image generation unit (also referred to as a "cross-sectional image acquisition unit") 930, a existence range calculation unit 935, an image combining unit 940, and a display control unit 950. The information processing system 900 is connected to a data server 990 that holds three-dimensional image data, error factor information described below, and any other suitable data. The information processing apparatus 900 is also connected to an ultrasonic diagnostic imaging apparatus serving as a second medical image collection device 980 configured to capture an ultrasonic tomographic image of an object.

[Acquisition of Three-Dimensional Image Data: Third Embodiment]

The three-dimensional image data held in the data server 990 may be an image obtained by capturing an image of an object in advance using a first medical image collection device 970 such as an MRI apparatus or an X-ray CT apparatus. In the following description, byway of example, an MRI apparatus is used as the first medical image collection device 970. In this embodiment, the three-dimensional image data is represented as three-dimensional volume data with each three-dimensional voxel representing a luminance value. In addition, the coordinates of each voxel is represented using the MRI apparatus coordinate system. The three-dimensional image data held in the data server 990 is acquired by the three-dimensional image data acquisition unit 920, and is input to the information processing apparatus 900.

[Acquisition of Region of Interest: Third Embodiment]

The data server 990 further holds information indicating a region of interest in the three-dimensional image data (which will be described in detail below). The information indicating the region of interest which is held in the data server 990 is acquired by the region-of-interest acquisition unit 922, and is input to the information processing apparatus 900. In the following description, by way of example, similarly to the three-dimensional image data, the information indicating the region of interest is also represented using the MRI apparatus coordinate system.

[Acquisition of Tomographic Image: Third Embodiment]

The ultrasonic diagnostic imaging apparatus serving as the second medical image collection device 980 captures ultrasonic tomographic images of an object in real time. The ultrasonic tomographic images are acquired by the tomographic image acquisition unit 910, and are sequentially input to the information processing apparatus 900. The position and posture of an ultrasonic probe are measured using a position and posture sensor (not illustrated), acquired by the position and posture acquisition unit 912, and input to the information processing apparatus 900. The position and posture of the ultrasonic probe are represented as a position and posture in the reference coordinate system with respect to, for example, the object. The position and posture acquisition unit 912 acquires the position and posture of the ultrasonic probe in the reference coordinate system, and calculates the position and posture of the ultrasonic tomographic image in the MRI apparatus coordinate system in accordance with the acquired position and posture.

[Calculation of Existence Range]

The existence range calculation unit 935 estimates a region (corresponding region) corresponding to the region of interest in the ultrasonic coordinate system on the basis of the information indicating the region of interest which is acquired by the region-of-interest acquisition unit 922 and the position and posture of the ultrasonic tomographic image which are acquired by the position and posture acquisition unit 912. The term "ultrasonic coordinate system", as used herein, refers to a three-dimensional coordinate system with respect to an ultrasonic tomographic image, and can be defined as, for example, a coordinate system whose origin is defined as one point in the tomographic image, with the x axis and y axis being set in a plane of the tomographic image and the z axis being set in a direction perpendicular to the plane. The existence range calculation unit 935 calculates the existence range of the corresponding region (second region) in the ultrasonic tomographic image on the basis of the estimated corresponding region and an estimated error value acquired by the error acquisition unit 923, which will be described below.

[Acquisition of Estimated Error Value: Third Embodiment]

The data server 990 holds, in addition to the information described above, information for calculating an estimated error value of the corresponding region (error factor information, which will be described in detail below). In other words, the error factor information is information for calculating the existence range of the corresponding region in the ultrasonic tomographic image. The error factor information held in the data server 990 is input to the information processing apparatus 900 through the error acquisition unit 923. The error acquisition unit 923 calculates an estimated error value of the corresponding region on the basis of the acquired error factor information. The calculated estimated error value is output to the existence range calculation unit 935.

[Generation of Cross-Sectional Image: Third Embodiment]

The cross-sectional image generation unit 930 receives the three-dimensional volume data output from the three-dimensional image data acquisition unit 920, and the position and posture of the ultrasonic tomographic image which are output from the position and posture acquisition unit 912. The cross-sectional image generation unit 930 generates a cross-sectional image corresponding to the ultrasonic tomographic image from the three-dimensional volume data on the basis of the received data, and outputs the generated cross-sectional image to the image combining unit 940. The image combining unit 940 acquires information indicating the existence range of the corresponding lesion (second region) from the existence range calculation unit 935, and draws the second region on top of the ultrasonic tomographic image acquired from the tomographic image acquisition unit 910. The image combining unit 940 further combines the resulting image with the cross-sectional image acquired from the cross-sectional image generation unit 930 (e.g., horizontally arranges the images side by side) to generate a composite image, and outputs the composite image to the display control unit 950 or to an external device. The display control unit 950 acquires the composite image output from the image combining unit 940, and displays the composite image on a display unit 960.

At least some of the units illustrated in FIG. 7 (i.e., the tomographic image acquisition unit 910, the position and posture acquisition unit 912, the three-dimensional image data acquisition unit 920, the region-of-interest acquisition unit 922, error acquisition unit 923, the cross-sectional image generation unit 930, the existence range calculation unit 935, the image combining unit 940, and the display control unit 950) may be implemented as independent devices. Alternatively, each of the individual units may be implemented by software for implementing the functions thereof by installing the unit into one or a plurality of computers and executing the software using a CPU in the computer. In this embodiment, it is assumed that the individual units are implemented by software, and are installed into a single computer.

[Basic Configuration of Computer: Third Embodiment]

FIG. 17 is a diagram illustrating the basic configuration of a computer that executes software to implement the functions of each of the tomographic image acquisition unit 910, the position and posture acquisition unit 912, the three-dimensional image data acquisition unit 920, the region-of-interest acquisition unit 922, the error acquisition unit 923, the cross-sectional image generation unit 930, the existence range calculation unit 935, the image combining unit 940, and the display control unit 950.

The CPU 1001 controls the overall operation of the computer using a program and data stored in the RAM 1002 or the ROM 1003. The CPU 1001 further controls the execution of software to implement the functions of each of the tomographic image acquisition unit 910, the position and posture acquisition unit 912, the three-dimensional image data acquisition unit 920, the region-of-interest acquisition unit 922, the error acquisition unit 923, the cross-sectional image generation unit 930, the existence range calculation unit 935, the image combining unit 940, and the display control unit 950.

The RAM 1002 has an area for temporarily storing a program and data loaded from the external storage device 1007 or the storage medium drive 1008, and also has a work area used when the CPU 1001 performs various processes.

The ROM 1003 generally stores programs, setting data, etc. of the computer. The keyboard 1004 and the mouse 1005 are input devices, and the operator can input various instructions to the CPU 1001 using the keyboard 1004 and the mouse 1005.

The display unit 1006 may be formed of a CRT display, a liquid crystal display, or any other suitable display, and corresponds to the display unit 960. The display unit 1006 can display the items to be displayed for image processing, such as a message and a GUI, as well as the composite image generated by the image combining unit 940.

The external storage device 1007 is a device functioning as a large-capacity information storage device such as a hard disk drive, and stores an OS, a program to be executed by the CPU 1001, and the like. In this embodiment, the "known information" is stored in the external storage device 1007, and is loaded into the RAM 1002 as necessary.

The storage medium drive 1008 reads a program and data stored in a storage medium such as a CD-ROM or a DVD-ROM in accordance with an instruction from the CPU 1001, and outputs the read program and data to the RAM 1002 and the external storage device 1007.

The I/F 1009 includes an analog video port or a digital input/output port such as an IEEE 1394 port, and an Ethernet (registered trademark) port through which information such as the composite image is output to outside. Data input to each port is captured into the RAM 1002 via the I/F 1009. Some of the functions of the tomographic image acquisition unit 910, the position and posture acquisition unit 912, the three-dimensional image data acquisition unit 920, the region-of-interest acquisition unit 922, and the error acquisition unit 923 are implemented by the I/F 1009.

The structural elements described above are connected to one another via the bus 1010.

Figure 9:
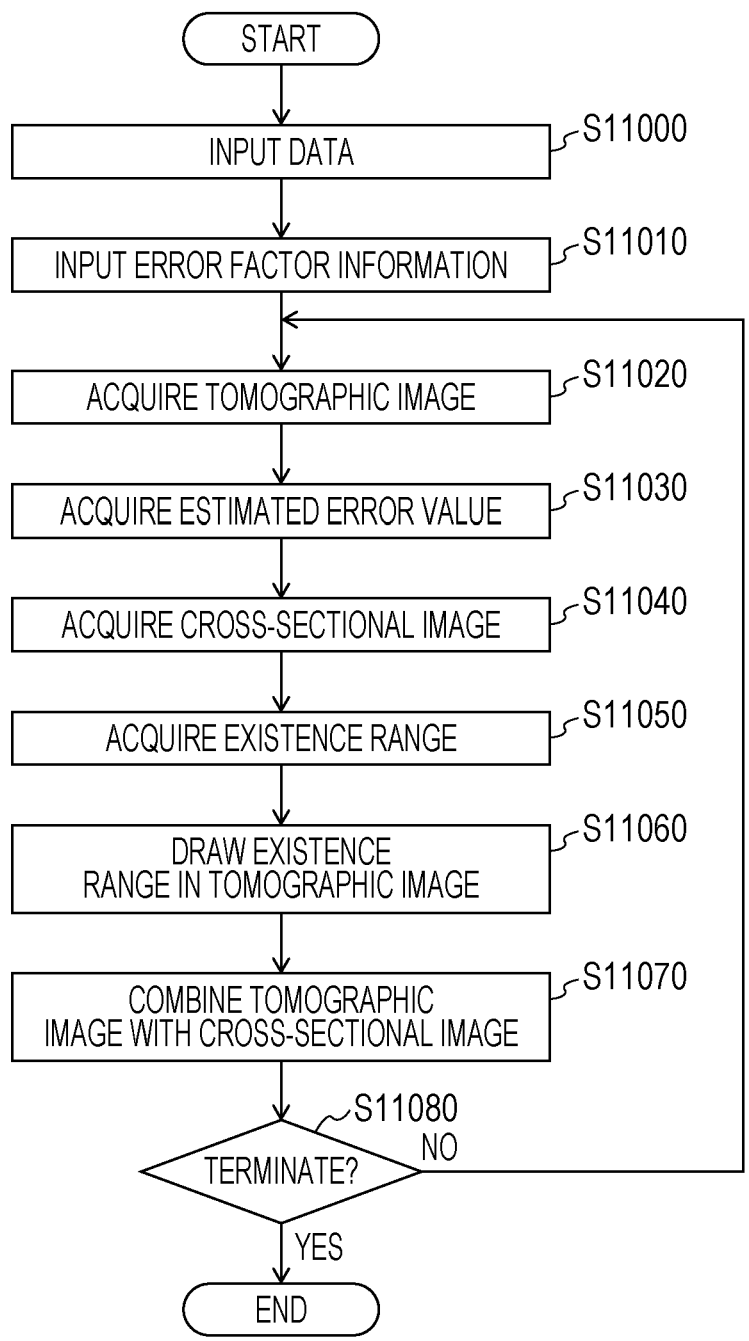
FIG. 9 is a flow diagram illustrating a processing procedure of the information processing apparatus according to the third embodiment.

FIG. 9 is a flowchart illustrating a whole processing procedure of the information processing apparatus 900. In this embodiment, the procedure in the flowchart is implemented by executing a program implementing the functions of the individual units by the CPU 1001. Before the following process is performed, a program code based on the flowchart has been loaded from, for example, the external storage device 1007 into the RAM 1002.

[S11000: Input of Data]

In step S11000, as a process of the three-dimensional image data acquisition unit 920, the information processing apparatus 900 acquires three-dimensional image data from the data server 990. Further, as a process of the region-of-interest acquisition unit 922, the information processing apparatus 900 acquires information indicating a region of interest from the data server 990. The information indicating the region of interest may be, for example, the position of the lesion of interest (the centroid of the region), or the coordinates of a group of points located in the boundary of the region of the lesion of interest.

[S11010: Input of Error Factor Information]

In step S11010, as a process of the error acquisition unit 923, the information processing apparatus 900 acquires from the data server 990 various kinds of error factor information (described below) to be used to calculate an estimated error value.

[S11020: Acquisition of Tomographic Image]

In step S11020, as a process of the tomographic image acquisition unit 910, the information processing apparatus 900 acquires an ultrasonic tomographic image from the second medical image collection device 980. Further, as a process of the position and posture acquisition unit 912, the information processing apparatus 900 acquires from the second medical image collection device 980 the position and posture of the ultrasonic probe obtained when the ultrasonic tomographic image is captured. The information processing apparatus 900 then calculates the position and posture of the ultrasonic tomographic image in the MRI apparatus coordinate system from the position and posture of the ultrasonic probe in the reference coordinate system by using the calibration data stored in advance as a known value.

[S11030: Acquisition of Estimated Error Value]

In step S11030, as a process of the error acquisition unit 923, the information processing apparatus 900 calculates an estimated error value on the basis of the various kinds of error factor information (various kinds of data used to calculate an error) acquired in step S11010.

In this embodiment, a relationship between the MRI apparatus coordinate system and the reference coordinate system is represented by a rigid-body transformation. However, an exact rigid-body transformation may not necessarily be provided between the position and posture of the object in the MRI apparatus coordinate system obtained when an MRI image is captured and the position and posture of the object in the reference coordinate system obtained in ultrasonic imaging is performed. Therefore, an error may exist when a relationship between the coordinate systems is represented by a rigid-body transformation. If a difference in position and posture of an object between the coordinate systems provides an exact rigid-body transformation, it is actually difficult to correctly determine the rigid-body transformation, and an error may exist. The error which may exist also includes an error in measured position and posture values acquired by the position and posture acquisition unit 912 (position and posture measurement error).

A process of calculating an estimated error value can be executed based on, for example, the characteristics of a position and posture sensor configured to measure the position and posture of the ultrasonic probe of the second medical image collection device 980. For example, a reference error value may be determined in advance for each measurement method of the position and posture sensor, and a value may be selected in accordance with the measurement method of the sensor to be used. For example, magnetic sensors generally have lower measurement accuracy than optical sensors. Thus, a smaller estimated error value can be calculated than an estimated error value calculated when information indicating that an optical sensor is in use is acquired as error factor information from the data server 990 and when a magnetic sensor is used on the basis of the acquired information. In addition, an estimated error value can be calculated, regardless of the difference between the measurement methods of the position and posture sensors, in accordance with a relationship of the spatial position and posture to a measurement standard of the position and posture sensor. For example, when the position and posture sensor is a magnetic sensor, an estimated error value can be defined as a function of the distance between the magnetic generator, or a measurement standard, and the ultrasonic probe, and a large value can be calculated as an estimated error value when the distance is large.

Also, when the position and posture sensor is an optical sensor, the positions of a plurality of indices (markers) disposed on the ultrasonic probe are measured using the optical sensor, and the position and posture of the ultrasonic probe is calculated on the basis of the measured positions. If the distribution of the plurality of indices is biased with respect to the optical sensor serving as a measurement standard, the error in the position and posture is large. Therefore, an estimated error value can be defined as a function of the distance between the optical sensor and the ultrasonic probe, and a large estimated error value can be calculated if the function has a large value. In addition, an estimated error value can be defined as a function of the angle between the vector pointing from the optical sensor towards the ultrasonic probe and the normal to the plane in which the plurality of indices are disposed, and a large estimated error value can be calculated if the function has a large value.

An estimated error value can also be calculated on the basis of a portion or the like of the object where the lesion of interest exists. For example, when the lesion of interest exists in the soft tissue of the breast or the like of the object, it is anticipated that this portion of the object may deform during a period between the capture time of the MRI image and the capture time of the ultrasonic image. Therefore, when the lesion of interest exists in the above portion, a large estimated error value can be calculated. Also, a large estimated error value can be calculated for the region of the heart and a region near the heart where a position varies largely due to heart beats or the region of the lung and a region near the lung where a position varies largely due to breathing. Specifically, information indicating a portion (the name of an organ or a position in an organ) in the object where the lesion of interest exists, and data (table) showing a correspondence between the portion and the magnitude of an error can be acquired as error factor information, and an estimated error value can be calculated on the basis of the above pieces of information.

An estimated error value can also be calculated so as to have a different value for each axial direction. For example, when the lesion of interest exists in the soft tissue of the breast or the like of the object, deformation undergoing a pressing force is likely to occur in the operating direction of the ultrasonic probe. Thus, a larger estimated error value can be calculated for the operating direction (than for two directions perpendicular to the operating direction). The operating direction of the ultrasonic probe can be calculated using a known method on the basis of the current and previous (e.g., 100 milliseconds ago) positions and postures of the ultrasonic probe. In this case, the estimated error value can be represented as three perpendicular vectors representing the direction and the magnitude.

In addition, information about the positions or the like of portions used as indices for calibration between the MRI apparatus coordinate system and the reference coordinate system can be acquired as error factor information, and an estimated error value can be calculated on the basis of relationships between these portions and the position of the lesion of interest. For example, if the xiphoid process of the object is used as an index used for the calibration, an estimated error value can be calculated as a function of the distance between the position of the xiphoid process in the MRI image and the lesion of interest. Also, if the position of the papilla is used as an index used for calibration, an estimated error value can be calculated as a function of the distance between the position of the papilla in the MRI image and the lesion of interest. Alternatively, an estimated error value may be acquired by estimating errors in a complex manner using a plurality of methods among the methods described above by way of example.

[S11040: Acquisition of Cross-Sectional Image]

In step S11040, as a process of the cross-sectional image generation unit 930, the information processing apparatus 900 generates a cross-sectional image of a reference image corresponding to the ultrasonic tomographic image obtained in step S11020. Specifically, a cross-sectional image obtained by cutting the same cross section as the ultrasonic tomographic image from the three-dimensional volume data obtained in step S11000 is generated in accordance with the position and posture of the ultrasonic tomographic image obtained in step S11020.

[S11050: Acquisition of Existence Range]

In step S11050, as a process of the existence range calculation unit 935, the information processing apparatus 900 calculates the existence range of the corresponding region in the ultrasonic tomographic image obtained in step S11020.

Specifically, first, the existence range calculation unit 935 estimates a corresponding region of the region of interest in the ultrasonic coordinate system. For example, if the position of a lesion of interest is given as information indicating the region of interest, the position of the corresponding lesion in the ultrasonic coordinate system is estimated as information indicating the corresponding region. If the coordinates of a group of points located in the boundary of the region of the lesion of interest is given as information indicating the region of interest, the coordinates of the group of points located in the boundary of the region of the corresponding lesion is estimated in the ultrasonic coordinate system as information indicating the corresponding region. The above estimation can be based on the position and posture of the ultrasonic tomographic image acquired by the position and posture acquisition unit 912.

Then, the existence range calculation unit 135 calculates the existence range of the corresponding region in the ultrasonic tomographic image on the basis of the estimated corresponding region and the estimated error value acquired in step S11030.

If the information indicating the corresponding region is the position of the corresponding lesion and the estimated error value does not depend on an axial direction, the three-dimensional existence range of the corresponding lesion in the ultrasonic coordinate system is defined as a sphere centered on the estimated position of the corresponding lesion and having a radius equal to the estimated error value. In addition, the existence range of the corresponding lesion in the ultrasonic tomographic image is defined as a circle that is a region (cross section of the sphere) where the sphere and the tomographic image intersect. Therefore, the existence range calculation unit 935 calculates, as the existence range of the corresponding lesion, the center position and the radius of the circle in the ultrasonic tomographic image. A method for calculating a region where a sphere defined in the three-dimensional space and a plane intersect is known, and the description thereof is thus omitted. When the sphere and the tomographic image do not intersect, information indicating "no existence ranges in the cross section" is stored.

If the information indicating the corresponding region is the position of the corresponding lesion and an estimated error value is given for each axial direction, the three-dimensional existence range of the corresponding lesion in the ultrasonic coordinate system is defined as an ellipsoid centered on the estimated position of the corresponding lesion and having a radius in each axial direction equal to the estimated error value in the corresponding axial direction. Therefore, the existence range calculation unit 935 calculates, as the existence range of the corresponding lesion in the ultrasonic tomographic image, a region (cross section of the ellipsoid) where the ellipsoid and the tomographic image intersect.

Meanwhile, if the information indicating the corresponding region is the coordinates of a group of points located in the boundary of the region of the corresponding lesion, a sphere or ellipsoid with a radius being an estimated error value is determined for each of the points using the method described above, and a region defined as a union of sets thereof can be defined as a three-dimensional existence range of a corresponding region. Therefore, the existence range calculation unit 935 calculates, as the existence range of the corresponding region in the tomographic image, a region where the region and the ultrasonic tomographic image intersect.

[S11060: Drawing of Existence Range in Tomographic Image]

In step S11060, as a process of the image combining unit 940, the information processing apparatus 900 draws information indicating the existence range of the corresponding lesion in the ultrasonic tomographic image calculated in step S11050, on top of the ultrasonic image. In this case, a range where the corresponding lesion may exist may be represented by a closed curve, a semi-transparent mask may be applied so as to surround the closed curve, and an ultrasonic tomographic image in an area inside the closed curve may be displayed in a normal manner. Thus, a search region within which the actual corresponding lesion is searched for can be clearly identified. In addition, the user can easily search for the actual corresponding lesion, and an efficient search can be achieved. A range where the corresponding lesion may exist may also be drawn with only a line of a closed curve. An area inside the range where the corresponding lesion may exist may be colored. In this case, the area may be transparent enough to search. As a result of the processing of step S11060, the ultrasonic tomographic image 503 illustrated in FIG. 5A in which the existence range 502 of the corresponding lesion 501 is overlaid on top of the tomographic image is generated. It is to be noted that if "no existence ranges in the cross section" is determined in step S11050, the processing of step S11060 is not executed.

Further, it may be determined whether or not the tomographic image intersects the corresponding region determined in step S11050, and, if the tomographic image intersects the corresponding region, an intersection region in the tomographic image may be displayed on top of the tomographic image.

[S11070: Combining of Tomographic Image and Cross-Sectional Image]

In step S11070, as a process of the image combining unit 940, the information processing apparatus 900 generates images in which the existence range of the corresponding lesion is overlaid on top of the cross-sectional image obtained in step S11040 and the ultrasonic tomographic image obtained in step S11060. For example, an image in which the above images are horizontally arranged side by side may be generated. Then, as a process of the display control unit 950, the information processing apparatus 900 displays the composite image on the display unit 960. The composite image is also output to an external device, if necessary, through the I/F 1009, and is also stored in the RAM 1002 so as to be available from another application.

[S11080: Determination of Termination of Whole Process]

In step S11080, the information processing apparatus 900 determines whether or not to terminate the whole process. For example, a termination instruction input by, for example, pressing a predetermined key (end key) on the keyboard 1004 by the operator is acquired. If it is determined that the process is to be terminated, the whole process of the information processing apparatus 900 ends. If it is determined that the process is not to be terminated, the process returns to step S11010, and the processing of step S11010 and subsequent steps is executed again on a new captured ultrasonic tomographic image.

Accordingly, the process of the information processing apparatus 900 is executed.

In the information processing apparatus according to this embodiment, therefore, an existence range of a corresponding lesion that takes an error in position estimation into account is presented on top of an ultrasonic tomographic image to help the operator search for the corresponding lesion. The presentation of the existence range of the corresponding lesion can reduce an undesired work of searching a range larger than necessary and can reduce the load on the operator during the search operation. Additionally, since the search range can be limited, the risk that the operator may perform erroneous association can be reduced.

In the embodiment described above, a cross-sectional image obtained by cutting the same cross section as an ultrasonic tomographic image serving as a reference image from three-dimensional image data is presented side by side with respect to the ultrasonic tomographic image. However, the cross-sectional image may not necessarily be displayed. In this case, the process of acquiring three-dimensional image data serving as a reference image and generating a cross-sectional image may not necessarily be performed.

Fourth Embodiment

The information processing system according to the third embodiment is based on the assumption that the shape of an object does not change between when three-dimensional image data is captured and when ultrasonic imaging is performed (i.e., the object is a rigid body). Further, a corresponding region (and the existence range thereof) of a region of interest in the ultrasonic coordinate system is estimated by measuring the position and posture of an ultrasonic probe with respect to the object. In contrast, an information processing system according to a fourth embodiment is configured to determine a corresponding region by estimating deformation from the shape of an object obtained when three-dimensional image data is captured to the shape of the object obtained when ultrasonic imaging is performed, in which the uncertainty of deformation estimation is taken into account to estimate an existence range of a corresponding region. The information processing system according to this embodiment will be described, focusing on the difference from the third embodiment.

Figure 8:
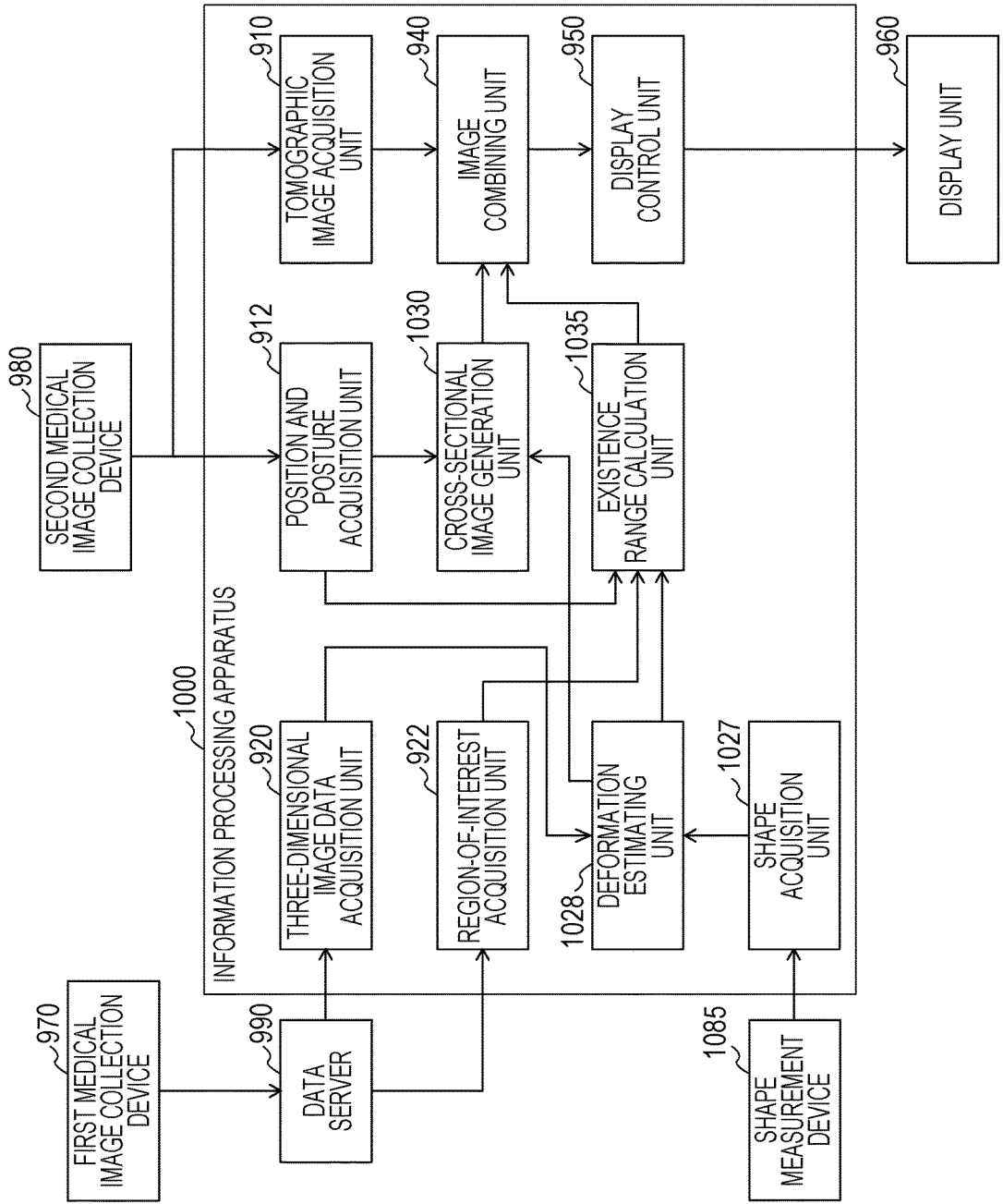
FIG. 8 is a diagram illustrating a device configuration of an information processing apparatus according to a fourth embodiment.

FIG. 8 illustrates the configuration of an information processing system according to this embodiment. In FIG. 8, substantially the same components as those in FIG. 7 are assigned the same reference numerals or symbols, and the descriptions thereof are omitted. As illustrated in FIG. 8, an information processing apparatus 1000 according to this embodiment is connected to a shape measurement device 1085.

A range sensor serving as the shape measurement device 1085 measures the surface shape of an object obtained when ultrasonic imaging is performed to obtain surface shape data. The shape measurement device 1085 may have any configuration so long as the shape measurement device 1085 is capable of measuring the shape of a target object, and may be, for example, a stereo image measurement device.

A shape acquisition unit 1027 acquires the surface shape data of the object input to the information processing apparatus 1000, and outputs the surface shape data to a deformation estimating unit 1028.

The deformation estimating unit 1028 estimates the deformed state of the object on the basis of the surface shape data acquired by the shape acquisition unit 1027. Further, the deformation estimating unit 1028 calculates a varying range of a deformation parameter (which will be described in detail below), and outputs the calculated range to an existence range calculation unit 1035. Further, the deformation estimating unit 1028 deforms the three-dimensional image data into the shape of the object obtained when ultrasonic imaging is performed to generate a deformed three-dimensional image, and outputs the deformed three-dimensional image to a cross-sectional image generation unit 1030.

The existence range calculation unit 1035 calculates the existence range of the corresponding region in the ultrasonic tomographic image on the basis of the information indicating the region of interest which is acquired by the region-of-interest acquisition unit 122 and the varying range of the deformation parameter estimated by the deformation estimating unit 1028.

The cross-sectional image generation unit 1030 generates a cross-sectional image corresponding to the ultrasonic tomographic image from the deformed three-dimensional image on the basis of the deformed three-dimensional image output from the deformation estimating unit 1028 and the position and posture of the ultrasonic tomographic image output from the position and posture acquisition unit 112, and outputs the generated cross-sectional image to the image combining unit 940.

Figure 10:
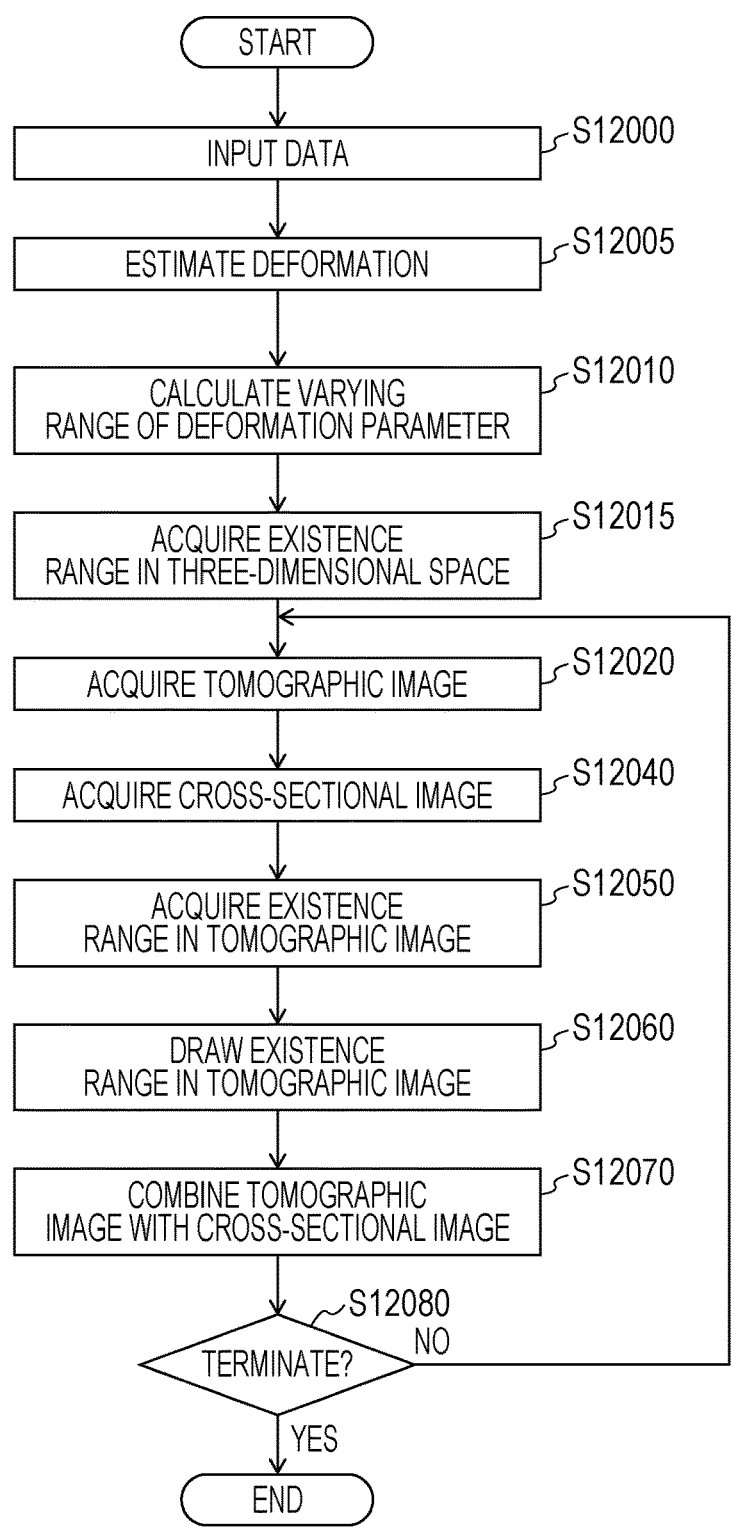
FIG. 10 is a flow diagram illustrating a processing procedure of the information processing apparatus according to the fourth embodiment.

FIG. 10 is a flowchart illustrating a whole processing procedure of the information processing apparatus 1000 according to this embodiment.

[S12000: Input of Data]

In step S12000, the information processing apparatus 1000 performs processing similar to that of step S11000 according to the third embodiment to acquire three-dimensional image data and information indicating a region of interest. Further, as a process of the shape acquisition unit 1027, the information processing apparatus 1000 acquires surface shape data of an object from the shape measurement device 1085.

[S12005: Deformation Estimation]

In step S12005, as a process of the deformation estimating unit 1028, the information processing apparatus 1000 estimates a deformed state of the object on the basis of the surface shape data acquired in step S12000. The information processing apparatus 1000 generates a deformation model of the object from the three-dimensional image data using, for example, a deformation estimation method described in Japanese Patent Laid-Open No. 2011-092263, and applies the deformation model to the shape data to estimate a deformation parameter. The information processing apparatus 1000 further deforms the three-dimensional image data into the shape of the object obtained when ultrasonic imaging is performed, in accordance with the estimated deformation parameter to generate a deformed three-dimensional image.

[S12010: Calculation of Varying Range of Deformation Parameter]

In step S12010, as a process of the deformation estimating unit 1028, the information processing apparatus 1000 calculates a varying range of the deformation parameter. The varying range of the deformation parameter refers to a parameter range defined such that the evaluation value of similarity between the shape data and the deformed shape falls within a certain range when the value of the deformation parameter is varied in the vicinity of an estimated value. The varying range represents the uncertainty of the estimated value of the deformation parameter.

[S12015: Calculation of Existence Range in Three-Dimensional Space]

In step S12015, as a process of the existence range calculation unit 1035, the information processing apparatus 1000 calculates an existence range of a corresponding region in the three-dimensional space on the basis of the uncertainty of the solution of deformation estimation. Specifically, the information processing apparatus 1000 varies the deformation parameter within the varying range determined in step S12010, and calculates displacements of the corresponding region caused by varying the deformation parameter. Further, a region containing all the regions obtained as a result of displacement is used as the existence range of the corresponding region in the three-dimensional space. For example, the smallest ellipsoid containing all the regions obtained as a result of displacement is derived, and is used as the existence range of the corresponding region.

[S12020: Acquisition of Tomographic Image]

In step S12020, the information processing apparatus 1000 performs processing similar to that of step S11020 according to the third embodiment to acquire an ultrasonic tomographic image and its position and posture.

[S12040: Acquisition of Cross-Sectional Image]

In step S12040, as a process of the cross-sectional image generation unit 1030, the information processing apparatus 1000 generates a cross-sectional image of the deformed three-dimensional image corresponding to the ultrasonic tomographic image obtained in step S12020.

[S12050: Acquisition of Existence Range in Cross-Sectional Image]

In step S12050, as a process of the existence range calculation unit 1035, the information processing apparatus 1000 calculates the existence range of the corresponding region in the ultrasonic tomographic image. Specifically, the existence range of the corresponding region in the three-dimensional space calculated in step S12015 is taken along the ultrasonic cross section to calculate the existence range of the corresponding region in the two-dimensional plane.

The processing of steps S12060, S12070, and S12080 is similar to the processing of steps S11060, S11070, and S11080 according to the third embodiment, respectively, and the descriptions thereof are thus omitted.

Therefore, the information processing apparatus according to this embodiment is configured to determine a corresponding region by estimating deformation from the shape of an object obtained when three-dimensional image data is captured to the shape of the object obtained when ultrasonic imaging is performed, in which the uncertainty of deformation estimation is taken into account to estimate the existence range of the corresponding region. Thus, even if the lesion of interest exists in the soft tissue of the breast or the like of the object, the user is able to obtain a more accurate search range for the actual corresponding region in the two-dimensional image, leading to more efficient search for the actual corresponding region.

First Modification of Fourth Embodiment

In this embodiment, a method for calculating the existence range of the corresponding region by taking the uncertainty of deformation estimation into account has been described in the context of a method based on a varying range of a parameter around the solution obtained in the estimation time of a deformation parameter. However, the present invention is not limited to this embodiment.

For example, the existence range of the corresponding region may be calculated on the basis of a variation of displacement of a region of interest obtained through a plurality of deformation simulations. For example, after the centroid of the lesion of interest is displaced by various modification simulations, a polyhedron including all the positions obtained as a result of displacement (e.g., a convex hull of all the positions) or a closed surface (e.g., an ellipsoid) can be calculated, and can be used as the existence range of the corresponding lesion.

Second Modification of Fourth Embodiment

In addition, even if, as in the fourth embodiment, deformation is taken into account, as in the third embodiment, an estimated error value may be acquired, and an existence range of a corresponding region may be calculated on the basis of the estimated error value.

For example, an existence range of a corresponding region may be calculated on the basis of an error distribution of deformation estimation for previous cases. For example, statistic values of errors may be held in a data server for respective sizes of the breasts and portions of lesions. In this case, information about the size of the breast of the object and the portion of the lesion can be acquired from an image, an associated statistic value can be acquired on the basis of the acquired information, and an existence range can be calculated using the acquired statistic value as an estimated error value.

An estimated error value can also be calculated on the basis of the residual obtained when the deformation estimating unit 1028 estimates a deformation parameter (or the divergence between the shape of the object obtained when ultrasonic imaging is performed and the shape of the deformed three-dimensional image). For example, if the residual is large, a large estimated error value can be calculated.

An estimated error value may also be changed in accordance with the deformation estimation method to be used. For example, a small estimated error value can be calculated when a high-accuracy deformation estimation method is to be used, and a large estimated error value can be calculated when a straightforward deformation estimation method is to be used.

Alternatively, the difference between a surface position of an ultrasonic probe and a body surface position in a cross-sectional image may be calculated, and an estimated error value may be calculated on the basis of the difference. For example, if the difference is large, a large estimated error value can be calculated.

An estimated error value may also be calculated on the basis of the reliability of image analysis to be performed as pre-processing of deformation estimation, such as body surface detection. For example, if the reliability of image analysis is low, a large estimated error value can be calculated.

In this modification, when one estimated error value is to be calculated, as in the third embodiment, the existence range of the corresponding lesion may be defined as a sphere centered on the position of the lesion of interest and having a radius equal to the estimated error value.

Fifth Embodiment

According to the embodiments described above, a range (two-dimensional region) where a corresponding lesion may exist in an ultrasonic tomographic image within a three-dimensional existence range including a portion (corresponding region, corresponding lesion) corresponding to a given portion (region of interest, lesion of interest) in three-dimensional image (reference image) data can be calculated by taking into account an error in position estimation. The term "three-dimensional existence range", as used herein, refers to a three-dimensional region where the corresponding lesion may exist, and is represented using the same space (coordinate system) as that of the ultrasonic tomographic image (target image). The existence range is presented on top of the ultrasonic tomographic image in order to help the user search for the corresponding lesion. This enables the user to obtain the range within which the corresponding lesion (search range) is searched for, and to efficiently search for and identify the corresponding lesion.

In the embodiment described above, however, only one cross section of a three-dimensional existence range of a corresponding lesion is displayed. Therefore, it is difficult to easily identify which portion of the three-dimensional existence range has been taken. For example, if the three-dimensional existence range is given in form of sphere, the two-dimensional existence range in the tomographic image is always displayed in a circular shape regardless of which portion in the three-dimensional existence range the ultrasonic tomographic image intersects. Therefore, it is not easy for a user who does not know the size of the sphere to determine whether the current intersection position is in a portion near the center of the sphere or in a portion near the edge of the sphere.

Accordingly, an information processing system according to a fifth embodiment is configured to display information indicating which location in a three-dimensional existence range has been taken as an ultrasonic tomographic image (e.g., color information associated with position information on the tomographic image), in addition to information (display style) indicating a two-dimensional region (intersection region). In this case, in accordance with position information on the tomographic image, a display style changing unit (an example of a display information generation unit 1137) changes the current display style to that indicating the two-dimensional region associated with the position information. This enables the user to easily grasp an overview of the three-dimensional existence range (three-dimensional region) and to efficiently search for and identify the corresponding lesion. A specifying unit (not illustrated) configured to manually or automatically specify a region of interest in a three-dimensional image may be provided. In addition, a determination unit (an example of the display information generation unit 1137) configured to determine, as a given region, an existence range where the corresponding region that corresponds to a region of interest exists may be provided.

Figure 11:
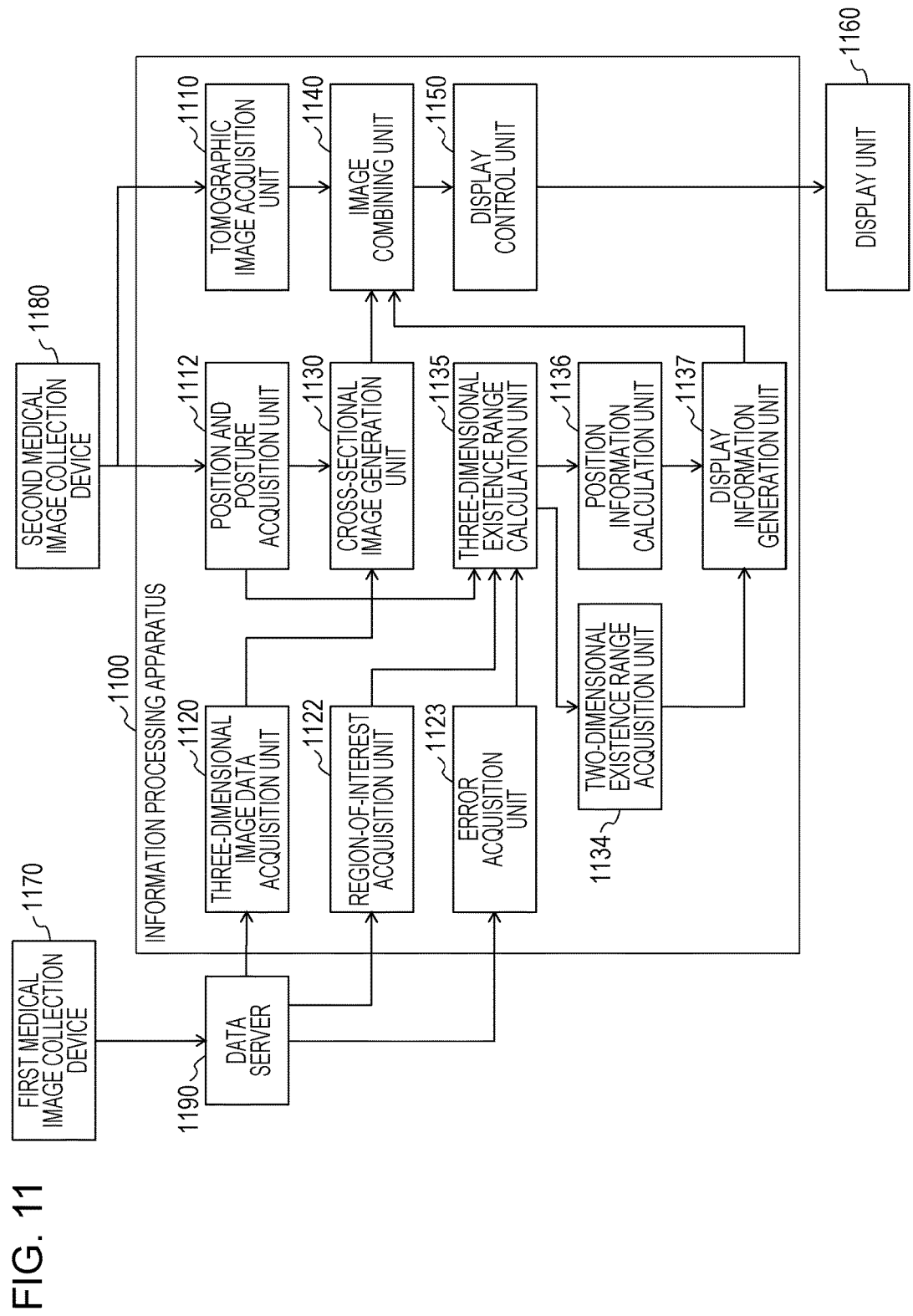
FIG. 11 is a diagram illustrating a device configuration of an information processing apparatus according to a fifth embodiment.

FIG. 11 illustrates the configuration of the information processing system according to this embodiment. An information processing apparatus 1100 according to this embodiment includes a tomographic image acquisition unit 1110, a position and posture acquisition unit 1112, a three-dimensional image data acquisition unit 1120 (also referred to as a "three-dimensional image acquisition unit"), a region-of-interest acquisition unit 1122, an error acquisition unit 1123, a cross-sectional image generation unit 1130, a three-dimensional existence range calculation unit (also referred to as a "three-dimensional region acquisition unit") 1135, a two-dimensional existence range acquisition unit (also referred to as a "two-dimensional region acquisition unit" or an "intersection region acquisition unit") 1134, a position information calculation unit 1136, an image combining unit 1140, and a display control unit 1150. The information processing apparatus 1100 is connected to a data server 1190 that holds three-dimensional image data, error factor information described below, and any other suitable data. The information processing apparatus 1100 is also connected to an ultrasonic diagnostic imaging apparatus serving as a second medical image collection device 1180 configured to capture an ultrasonic tomographic image of an object.

[Acquisition of Three-Dimensional Image Data: Fifth Embodiment]

The three-dimensional image data held in the data server 1190 may be an image obtained by capturing an image of an object in advance using a first medical image collection device 1170 such as an MRI apparatus or an X-ray CT apparatus. In the following description, byway of example, an MRI apparatus is used as the first medical image collection device 1170. In this embodiment, the three-dimensional image data is represented as three-dimensional volume data with each three-dimensional voxel representing a luminance value. In addition, the coordinates of each voxel is represented using the MRI apparatus coordinate system. The three-dimensional image data held in data server 1190 is acquired by the three-dimensional image data acquisition unit 1120, and is input to the information processing apparatus 1100.

[Acquisition of Region of Interest: Fifth Embodiment]

The data server 1190 further holds information indicating a region of interest in the three-dimensional image data (which will be described in detail below). The information indicating the region of interest which is held in the data server 1190 is acquired by the region-of-interest acquisition unit 1122, and is input to the information processing apparatus 1100. In the following description, byway of example, similarly to the three-dimensional image data, the information indicating the region of interest is also represented using the MRI apparatus coordinate system.

[Acquisition of Tomographic Image: Fifth Embodiment]

The ultrasonic diagnostic imaging apparatus serving as the second medical image collection device 1180 captures ultrasonic tomographic images of an object in real time. The ultrasonic tomographic images are acquired by the tomographic image acquisition unit 1110, and are sequentially input to the information processing apparatus 1100. The position and posture of an ultrasonic probe are measured using a position and posture sensor (not illustrated), acquired by the position and posture acquisition unit 1112, and input to the information processing apparatus 1100. The position and posture of the ultrasonic probe are represented as a position and posture in the reference coordinate system with respect to, for example, the object. The position and posture acquisition unit 1112 acquires the position and posture of the ultrasonic probe in the reference coordinate system, and calculates the position and posture of the ultrasonic tomographic image in the MRI apparatus coordinate system in accordance with the acquired position and posture.

[Calculation of Three-Dimensional Existence Range]

The three-dimensional existence range calculation unit 1135 estimates a region (corresponding region) corresponding to the region of interest in the ultrasonic coordinate system on the basis of the information indicating the region of interest which is acquired by the region-of-interest acquisition unit 1122 and the position and posture of the ultrasonic tomographic image which are acquired by the position and posture acquisition unit 1112. The term "ultrasonic coordinate system", as used herein, refers to a three-dimensional coordinate system with respect to an ultrasonic tomographic image, and can be defined as, for example, a coordinate system whose origin is defined as one point in the tomographic image, with the x axis and y axis being set in a plane of the tomographic image and the z axis being set in a direction perpendicular to the plane. The three-dimensional existence range calculation unit 1135 calculates a three-dimensional existence range (three-dimensional region in this embodiment) of the corresponding region in the ultrasonic coordinate system on the basis of the estimated corresponding region and an estimated error value acquired by the error acquisition unit 1123, which will be described below.

[Acquisition of Two-Dimensional Existence Range]

The two-dimensional existence range acquisition unit 1134 determines an intersection region between the ultrasonic tomographic image and the three-dimensional existence range on the basis of the three-dimensional existence range calculated by the three-dimensional existence range calculation unit 1135, and outputs the determined intersection region to the display information generation unit 1137 as a two-dimensional existence range of the corresponding region in the ultrasonic tomographic image.

[Calculation of Position Information]

The position information calculation unit 1136 calculates relative position information on the ultrasonic tomographic image with respect to the three-dimensional existence range on the basis of the information indicating the three-dimensional existence range of the corresponding region in the ultrasonic coordinate system which is acquired from the three-dimensional existence range calculation unit 1135 and the information about the position and posture of the ultrasonic tomographic image. The position information calculation unit 1136 outputs the calculated relative position information to the display information generation unit 1137.

[Generation of Display Information about Existence Range]

The display information generation unit 1137 generates display information about the two-dimensional existence range to which the relative position information has been added, on the basis of the information about the two-dimensional existence range which is acquired from the two-dimensional existence range acquisition unit 1134 and the relative position information about the ultrasonic tomographic image which is acquired from the position information calculation unit 1136.

[Acquisition of Estimated Error Value: Fifth Embodiment]

The data server 1190 holds, in addition to the information described above, information for calculating an estimated error value of the corresponding region (error factor information, which will be described in detail below). In other words, the error factor information is information for calculating a three-dimensional existence range of the corresponding region in the ultrasonic tomographic image. The error factor information held in the data server 1190 is input to the information processing apparatus 1100 through the error acquisition unit 1123. The error acquisition unit 1123 calculates an estimated error value of the corresponding region on the basis of the acquired error factor information. The calculated estimated error value is output to the three-dimensional existence range calculation unit 1135.

[Generation of Cross-Sectional Image: Fifth Embodiment]

The cross-sectional image generation unit 1130 receives the three-dimensional volume data output from the three-dimensional image data acquisition unit 1120, and the position and posture of the ultrasonic tomographic image output from the position and posture acquisition unit 1112. The cross-sectional image generation unit 1130 generates a cross-sectional image corresponding to the ultrasonic tomographic image from the three-dimensional volume data on the basis of the received data, and outputs the generated cross-sectional image to the image combining unit 1140. The image combining unit 1140 acquires display information about the two-dimensional existence range from the display information generation unit 1137, and draws the two-dimensional existence range on top of the ultrasonic tomographic image acquired from the tomographic image acquisition unit 1110. The image combining unit 1140 further combines the resulting image with the cross-sectional image acquired from the cross-sectional image generation unit 1130 (e.g., horizontally arranges the images side by side) to generate a composite image, and outputs the composite image to the display control unit 1150 or to an external device. The display control unit 1150 acquires the composite image output from the image combining unit 1140, and displays the composite image on a display unit 1160.

At least some of the units illustrated in FIG. 11 (i.e., the tomographic image acquisition unit 1110, the position and posture acquisition unit 1112, the three-dimensional image data acquisition unit 1120, the region-of-interest acquisition unit 1122, the error acquisition unit 1123, the cross-sectional image generation unit 1130, the three-dimensional existence range calculation unit 1135, the two-dimensional existence range acquisition unit 1134, the position information calculation unit 1136, the display information generation unit 1137, the image combining unit 1140, and the display control unit 1150) may be implemented as independent devices. Alternatively, each of the individual units may be implemented by software for implementing the functions thereof by installing the unit into one or a plurality of computers and executing the software using a CPU in the computer. In this embodiment, it is assumed that the individual units are implemented by software, and are installed into a single computer.

[Basic Configuration of Computer: Fourth Embodiment]

FIG. 17 is a diagram illustrating the basic configuration of a computer that executes software to implement the functions of each of the tomographic image acquisition unit 1110, the position and posture acquisition unit 1112, the three-dimensional image data acquisition unit 1120, the region-of-interest acquisition unit 1122, the error acquisition unit 1123, the cross-sectional image generation unit 1130, the three-dimensional existence range calculation unit 1135, the two-dimensional existence range acquisition unit 1134, the position information calculation unit 1136, the display information generation unit 1137, the image combining unit 1140, and the display control unit 1150.

The CPU 1001 controls the overall operation of the computer using a program and data stored in the RAM 1002 or the ROM 1003. The CPU 1001 further controls the execution of software to implement the functions of each of the tomographic image acquisition unit 1110, the position and posture acquisition unit 1112, the three-dimensional image data acquisition unit 1120, the region-of-interest acquisition unit 1122, the error acquisition unit 1123, the cross-sectional image generation unit 1130, the three-dimensional existence range calculation unit 1135, the two-dimensional existence range acquisition unit 1134, the position information calculation unit 1136, the display information generation unit 1137, the image combining unit 1140, and the display control unit 1150.

The RAM 1002 has an area for temporarily storing a program and data loaded from the external storage device 1007 or the storage medium drive 1008, and also has a work area used when the CPU 1001 performs various processes.

The ROM 1003 generally stores programs, setting data, etc. of the computer. The keyboard 1004 and the mouse 1005 are input devices, and a user can input various instructions to the CPU 1001 using the keyboard 1004 and the mouse 1005.

The display unit 1006 may be formed of a CRT display, a liquid crystal display, or any other suitable display, and corresponds to the display unit 1160. The display unit 1006 can display the items to be displayed for image processing, such as a message and a GUI, as well as the composite image generated by the image combining unit 1140.

The external storage device 1007 is a device functioning as a large-capacity information storage device such as a hard disk drive, and stores an OS, a program to be executed by the CPU 1001, and the like. In this embodiment, the "known information" is stored in the external storage device 1007, and is loaded into the RAM 1002 as necessary.

The storage medium drive 1008 reads a program and data stored in a storage medium such as a CD-ROM or a DVD-ROM in accordance with an instruction from the CPU 1001, and outputs the read program and data to the RAM 1002 and the external storage device 1007.

The I/F 1009 includes an analog video port or a digital input/output port such as an IEEE 1394 port, and an Ethernet (registered trademark) port through which information such as the composite image is output to outside. Data input to each port is captured into the RAM 1002 via the I/F 1009. Some of the functions of the tomographic image acquisition unit 1110, the position and posture acquisition unit 1112, the three-dimensional image data acquisition unit 1120, the region-of-interest acquisition unit 1122, and the error acquisition unit 1123 are implemented by the I/F 1009.

The structural elements described above are connected to one another via the bus 1010.

Figure 12:
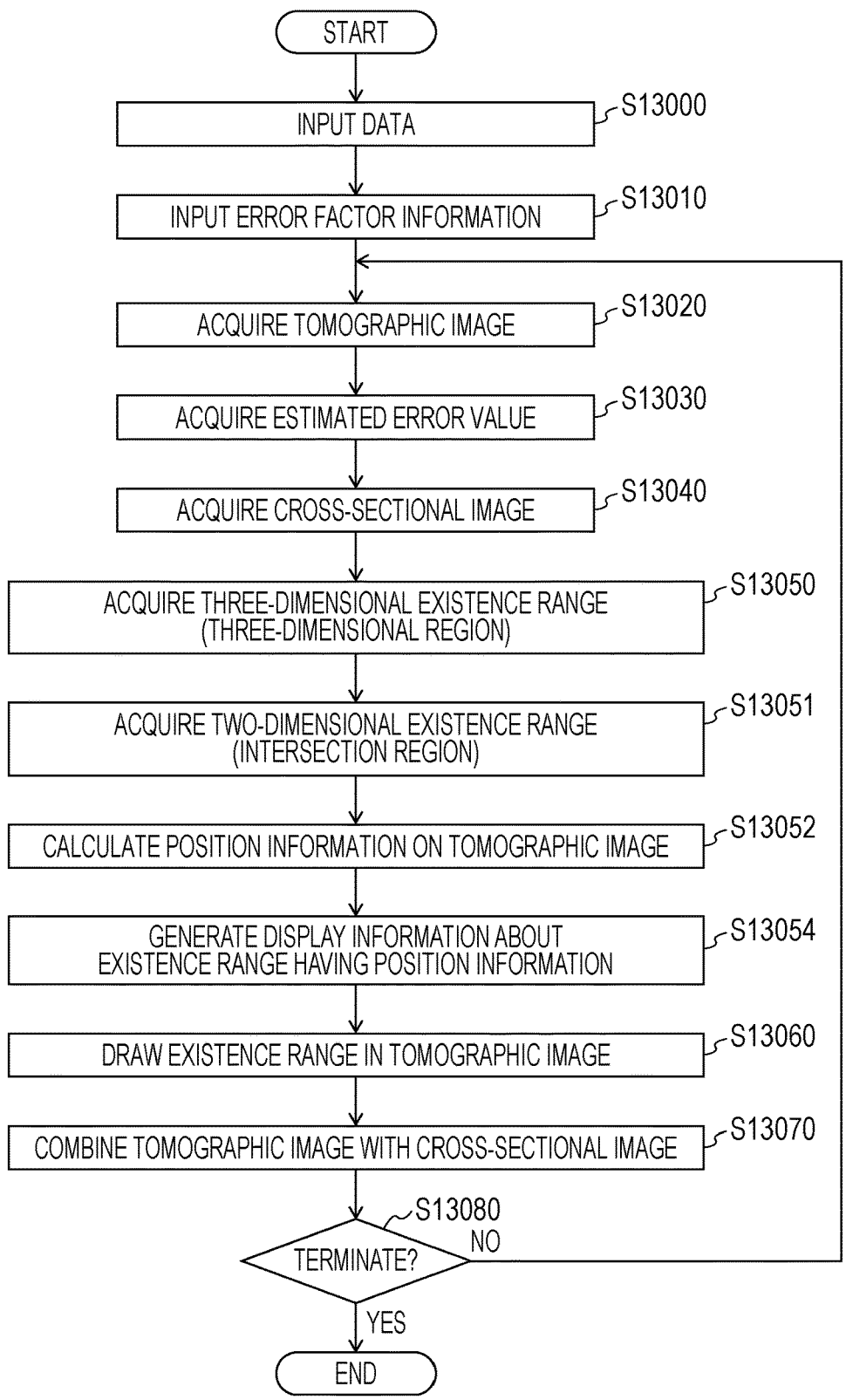
FIG. 12 is a flow diagram illustrating a processing procedure of the information processing apparatus according to the fifth embodiment.

FIG. 12 is a flowchart illustrating a whole processing procedure of the information processing apparatus 1100. In this embodiment, the procedure in the flowchart is implemented by executing a program implementing the functions of the individual units by the CPU 1001. Before the following process is performed, a program code based on the flowchart has been loaded from, for example, the external storage device 1007 into the RAM 1002.

[S13000: Input of Data]

In step S13000, as a process of the three-dimensional image data acquisition unit 1120, the information processing apparatus 1100 acquires three-dimensional image data from the data server 1190. Further, as a process of the region-of-interest acquisition unit 1122, the information processing apparatus 1100 acquires information indicating a region of interest from the data server 1190. The information indicating the region of interest may be, for example, the position of the lesion of interest (the centroid of the region), or the coordinates of a group of points located in the boundary of the region of the lesion of interest.

[S13010: Input of Error Factor Information]

In step S13010, as a process of the error acquisition unit 1123, the information processing apparatus 1100 acquires from the data server 1190 various kinds of error factor information to be used to calculate an estimated error value. The error factor information may be information for calculating the existence range of the corresponding region in the ultrasonic tomographic image. For example, information indicating the type of the position and posture sensor (such as a sensor A or a sensor B) to be used to measure the position and posture of the ultrasonic probe is acquired as error factor information from the data server 1190.

[S13020: Acquisition of Tomographic Image]

In step S13020, as a process of the tomographic image acquisition unit 1110, the information processing apparatus 1100 acquires an ultrasonic tomographic image from the second medical image collection device 1180. Further, as a process of the position and posture acquisition unit 1112, the information processing apparatus 1100 acquires from the second medical image collection device 1180 the position and posture of the ultrasonic probe obtained when the ultrasonic tomographic image is captured. The information processing apparatus 1100 then calculates the position and posture of the ultrasonic tomographic image in the MRI apparatus coordinate system from the position and posture of the ultrasonic probe in the reference coordinate system by using the calibration data stored in advance as a known value.

[S13030: Acquisition of Estimated Error Value]

In step S13030, as a process of the error acquisition unit 1123, the information processing apparatus 1100 calculates an estimated error value on the basis of the various kinds of error factor information (various kinds of data used to calculate an error) acquired in step S13010, and outputs the calculated estimated error value to the three-dimensional existence range calculation unit 1135.

A process of calculating an estimated error value can be executed based on, for example, the characteristics of a position and posture sensor configured to measure the position and posture of the ultrasonic probe. A reference error value may be determined in advance for each type of position and posture sensor, and a value may be selected in accordance with the type of sensor to be used. For example, if the error factor information obtained in step S13010 is information indicating that a sensor A, which is an optical sensor, is in use, a smaller estimated error value can be calculated than that calculated when a sensor B, which is a magnetic sensor, is in use. The process of estimating an error may be performed using any other method.

[S13040: Acquisition of Cross-Sectional Image]

In step S13040, as a process of the cross-sectional image generation unit 1130, the information processing apparatus 1100 generates a cross-sectional image of a reference image corresponding to the ultrasonic tomographic image obtained in step S13020. Specifically, a cross-sectional image obtained by cutting the same cross section as the ultrasonic tomographic image from the three-dimensional volume data obtained in step S13000 is generated in accordance with the position and posture of the ultrasonic tomographic image obtained in step S13020.

[S13050: Acquisition of Three-Dimensional Existence Range]

In step S13050, as a process of the three-dimensional existence range calculation unit 1135, the information processing apparatus 1100 calculates a three-dimensional existence range (three-dimensional region) of the corresponding region in the ultrasonic coordinate system of the ultrasonic tomographic image obtained in step S13020.

Specifically, first, the three-dimensional existence range calculation unit 1135 estimates a corresponding region of the region of interest in the ultrasonic coordinate system. For example, if the position of a lesion of interest is given as information indicating the region of interest, the position of the corresponding lesion in the ultrasonic coordinate system is estimated as information indicating the corresponding region.

Then, the three-dimensional existence range calculation unit 1135 calculates a three-dimensional existence range of the corresponding region in the ultrasonic coordinate system on the basis of the estimated corresponding region and the estimated error value acquired in step S13030. For example, if the information indicating the corresponding region is the position of the corresponding lesion and the estimated error value does not depend on an axial direction, the three-dimensional existence range of the corresponding lesion in the ultrasonic coordinate system is calculated as a sphere centered on the estimated position of the corresponding lesion and having a radius equal to the estimated error value.

[S13051: Acquisition of Two-Dimensional Existence Range]

In step S13051, as a process of the two-dimensional existence range acquisition unit 1134, the information processing apparatus 1100 determines an intersection region (two-dimensional existence range) between the ultrasonic tomographic image and the three-dimensional existence range on the basis of the three-dimensional existence range calculated by the three-dimensional existence range calculation unit 1135, and outputs the intersection region to the display information generation unit 1137. If the three-dimensional existence range is a sphere, the two-dimensional existence range is defined as a circle that is a region (cross section of the sphere) where the sphere and the tomographic image intersect. Therefore, the two-dimensional existence range acquisition unit 1134 calculates, as a two-dimensional existence range, the center position and the radius of the circle in the ultrasonic tomographic image. A method for calculating an intersection region between a sphere defined in the three-dimensional space and a plane is known, and the description thereof is thus omitted. If the sphere and the tomographic image do not intersect, information indicating "no existence ranges in the cross section" is stored.

[S13052: Calculation of Position Information on Tomographic Image]

In step S13052, as a process of the position information calculation unit 1136, the information processing apparatus 1100 acquires the three-dimensional existence range and the position information on the ultrasonic tomographic image from the three-dimensional existence range calculation unit 1135, and calculates relative position information about the ultrasonic tomographic image with respect to the three-dimensional existence range. It is to be noted that if "no existence ranges in the cross section" is determined in step S13051, the processing of step S13052 is not executed. A specific calculation method will now be described.

Figure 13:
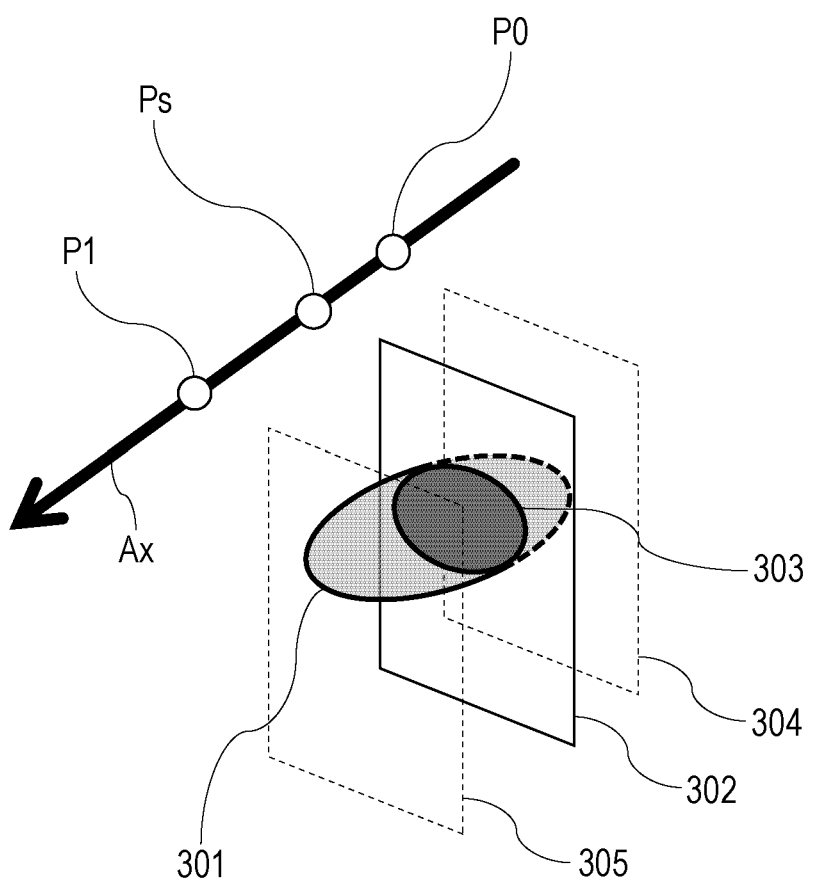
FIG. 13 is a diagram illustrating position information about an ultrasonic tomographic image in a three-dimensional existence range.

FIG. 13 is a diagram illustrating position information on an ultrasonic tomographic image in a three-dimensional existence range. Reference numeral 301 denotes a three-dimensional existence range calculated in step S13050, reference numeral 302 denotes an ultrasonic tomographic image, and reference numeral 303 denotes a two-dimensional existence range obtained by cutting the three-dimensional existence range 301 by the ultrasonic cross ultrasonic tomographic image 302.

The information processing apparatus 1100 sets a plane (hereinafter referred to as the "parallel plane") parallel to the ultrasonic tomographic image 302 in the three-dimensional space. When the set parallel plane is translated along an axis perpendicular to the ultrasonic tomographic image 302, the position at which the parallel plane starts to intersect the three-dimensional existence range 301 and the position at which the intersection ends are calculated. The position at which the intersection starts is defined as a start position (an example of a given position), and the position at which the intersection ends is defined as an end position (an example of a given position). Reference numeral 304 denotes the start position and the reference numeral 305 denotes the end position.

Then, the information processing apparatus 1100 plots a position corresponding to the ultrasonic tomographic image 302, a position corresponding to the start position, and a position corresponding to the end position along an axis perpendicular to the ultrasonic tomographic image 302, and defines them as a tomographic image corresponding position, a start corresponding position, and an end corresponding position, respectively. Reference symbol Ax denotes an orthogonal axis perpendicular to the ultrasonic tomographic image 302, reference symbol Ps denotes the tomographic image corresponding position, reference symbol P0 denotes the start corresponding position, and reference symbol P1 denotes the end corresponding position. A relative position (positional relationship) for the tomographic image corresponding position Ps, which is located between the start corresponding position P0 and the end corresponding position P1, is calculated as relative position information. In this embodiment, when normalization is performed so that, for example, the coordinates of the positions P0 and P1 along the axis Ax are equal to 0 and 1, respectively, the coordinates (e.g., 0.3) of the tomographic image corresponding position Ps therebetween are defined as the relative position information.

In this manner, the start position 304 and the end position 305 of the three-dimensional existence range 301 are determined along the axis perpendicular to the ultrasonic tomographic image 302, and relative position information about the ultrasonic tomographic image 302 between the positions 304 and 305 is calculated. This implies that when translating an ultrasonic probe while fixing the posture of the currently displayed ultrasonic tomographic image 302, the user determines relative position information about the current ultrasonic tomographic image 302 with respect to the position at which the ultrasonic probe starts to intersect the three-dimensional existence range and the position at which the intersection ends. Therefore, the user is able to easily determine in which direction and to what degree to translate the ultrasonic probe while fixing the posture of the ultrasonic tomographic image 302 until which edge of the three-dimensional existence range 301 the ultrasonic probe will reach.

It is to be understood that the method of calculating the start position and the end position is not limited to a method in which a parallel plane is translated along an axis perpendicular to an ultrasonic tomographic image. The start position and the end position may be determined by, for example, translating the parallel plane along an arbitrary axis and calculating a position at which the parallel plane starts to intersect the three-dimensional existence range 301 and a position at which the intersection ends.

The calculated relative position information is transmitted to the display information generation unit 1137.

[S13054: Generation of Display Information about Existence Range Having Position Information]

In step S13054, as a process of the display information generation unit 1137, the information processing apparatus 1100 generates display information in which relative position information is added to a two-dimensional existence range, on the basis of the shape information indicating the contour of the two-dimensional existence range, which is acquired from the two-dimensional existence range acquisition unit 1134, and the relative position information about the ultrasonic tomographic image, which is acquired from the position information calculation unit 1136. It is to be noted that if "no existence ranges in the cross section" is determined in step S13051, the processing of step S13054 is not executed. A specific generation method will now be described.

First, the information processing apparatus 1100 associates relative position information about an ultrasonic tomographic image with a color table, thereby obtaining color information corresponding to the position of the ultrasonic tomographic image in the three-dimensional existence range.

Figure 14A:
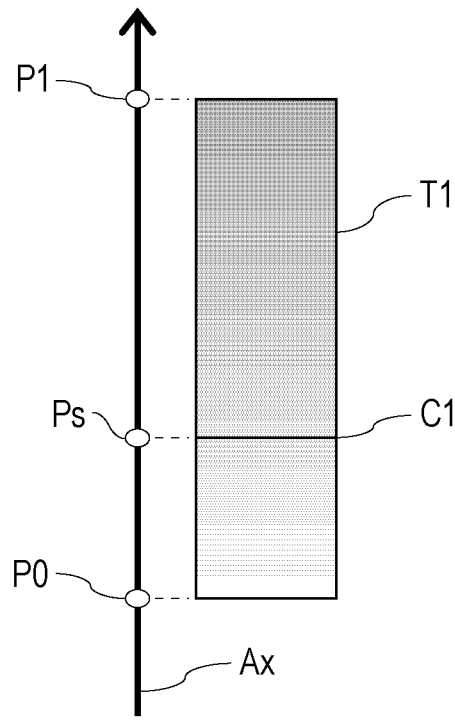
FIG. 14A is a diagram illustrating the association of relative position information with a color table.

FIG. 14A is a diagram illustrating the association of relative position information with a color table. Reference symbols Ax, Ps, P1, and P2 represent items similar to those illustrated in FIG. 13. A color table with colors changing (modified) between the positions P0 and P1 along the axis Ax in accordance with the position. In this embodiment, for example, a color table with continuous changes in the intensity of a specific color such that the nearer the position P0, the lighter the color and the nearer the position P1, the darker the color. Then, color information on the color table corresponding to the relative position information about the ultrasonic tomographic image which has been normalized in a range between the positions P0 and P1 in step S13054 is acquired. Reference symbol T1 denotes a color table, and reference symbol C1 denotes color information corresponding to the relative position information. For example, if the color table T1 represents a color table with changes in the intensity of blue (light blue becomes darker blue in the direction from the position P0 to the position P1) and the relative position information about the position Ps is 0.3, the position Ps is mapped onto a position on the color table T1 which is near the position P0. Therefore, the color information C1 is represented in slightly light blue. By referring to this color information, the user can intuitively understand that the tomographic image corresponding position Ps is comparatively close to the position P0.

However, the method for setting a color table is not limited to the method described above. For example, a color table with stepwise changes (e.g., ten levels), instead of continuous changes, in the intensity of a specific color may be used. Alternatively, a color table in which a plurality of typical colors, instead of a single color, are arranged between the positions P0 and P1 with certain intervals and in which continuous changes occur between adjacent colors (e.g., black, blue, green, yellow, red, and white, in this order, in the direction from the position P0 to the position P1) may be used. A color table in which the distance between the positions P0 and P1 is divided into a plurality of sections, each of which is assigned a different color, may also be used.

Then, the information processing apparatus 1100 generates display information associated with shape information about the two-dimensional existence range, on the basis of the color information corresponding to the acquired relative position information about the ultrasonic tomographic image. The generated display information is referred to as existence range display information. In this embodiment, display information in which the acquired color information is added to the shape of the contour of the two-dimensional existence range is obtained.

Figure 15A:
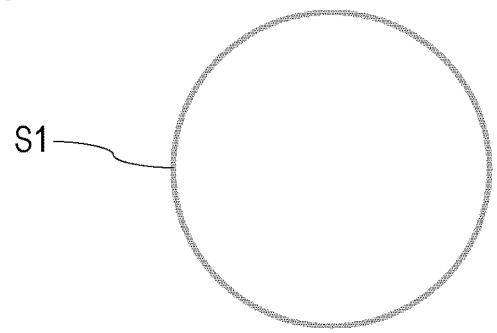
FIG. 15A is a diagram illustrating existence range display information.

FIGS. 15A to 15D are diagrams illustrating existence range display information. FIG. 15A illustrates display information in which color information is added to the shape of the contour (contour line) of an existence range. In FIG. 15A, reference symbol S1 denotes the shape of the contour (contour line) of an existence range to which color information is added. For example, if the relative position information is 0.3 and is mapped onto, as described above, slightly light blue, the shape of the contour (contour line) S1 is colored slightly light blue.

Figure 15B:
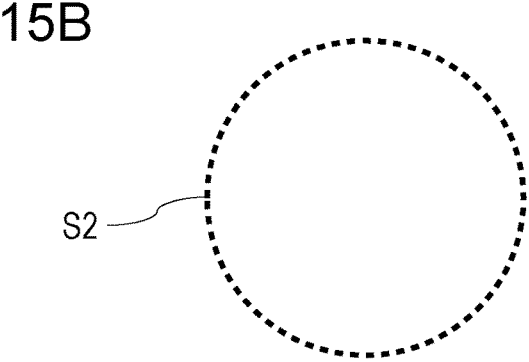
FIG. 15B is a diagram illustrating existence range display information.

However, the method of generating existence range display information is not limited to the method described above. For example, instead of relative position information about the ultrasonic tomographic image being added to shape information about the two-dimensional existence range as color information, a curve representing a shape may be indicated by a dotted line, and may be represented with the density of the dotted line. In this case, instead of a color table, a table with changes in the density of a dotted line between the positions P0 and P1 in accordance with the position is set in advance (e.g., a coarse dotted line is changed to a fine dotted line in the direction from the position P0 to the position P1), and the position Ps is mapped onto the table. FIG. 15B illustrates display information in which dotted line density information is added to the shape of the contour of the existence range. In FIG. 15B, reference symbol S2 denotes the shape of the existence range to which dotted line density information is added. For example, if the relative position information is also 0.3 and is mapped onto a slightly coarse dotted line, the shape of the contour S2 is drawn with a slightly coarse dotted line.

Figure 15C:
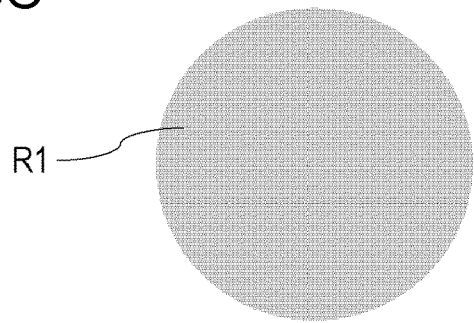
FIG. 15C is a diagram illustrating existence range display information.
Figure 15D:
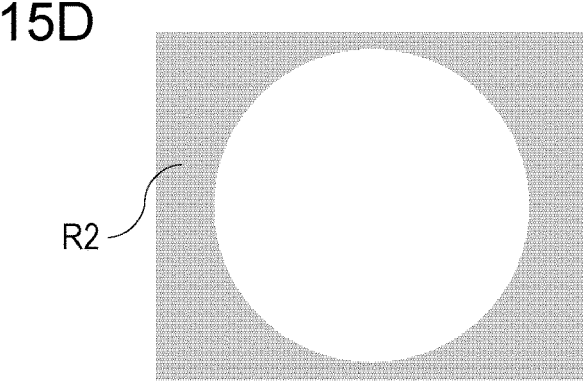
FIG. 15D is a diagram illustrating existence range display information.

The object to which relative position information about an ultrasonic tomographic image is added is not limited to the shape of the contour of a two-dimensional existence range. For example, an inner region of a two-dimensional existence range may be colored. FIG. 15C illustrates display information in which color information is added to an inner region of an existence range. In FIG. 15C, reference symbol R1 denotes an inner region of an existence range to which color information has been added. For example, as described above, if the relative position information is mapped onto slightly light blue, the inner region R1 is a region colored slightly light blue. Conversely, an outer region of the two-dimensional existence range may be colored. FIG. 15D illustrates display information in which color information is added to an outer region of the existence range. In FIG. 15D, reference symbol R2 denotes an outer region of the existence range to which color information has been added. Mapping onto a color similar to that described above would allow the outer region R2 to be colored slightly light blue. The generated existence range display information is transmitted to the image combining unit 1140.

[S13060: Drawing of Existence Range in Tomographic Image]

In step S13060, as a process of the image combining unit 1140, the information processing apparatus 1100 draws existence range display information in which the relative position information about the ultrasonic tomographic image is added to the two-dimensional existence range of the corresponding lesion, which is acquired from the display information generation unit 1137, on top of the ultrasonic image. It is to be noted that if "no existence ranges in the cross section" is determined in step S13051, the processing of step S13060 is not executed.

Figure 16A:
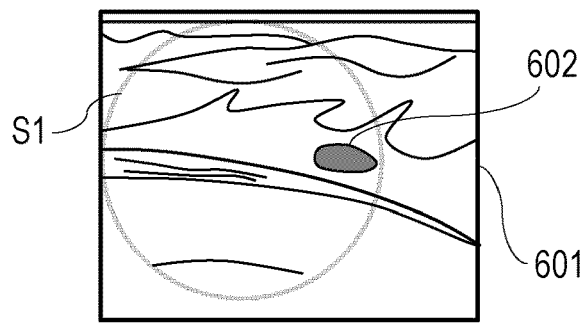
FIG. 16A is a diagram illustrating an ultrasonic tomographic image on which existence range display information is superimposed and displayed.

FIGS. 16A to 16D are diagrams illustrating ultrasonic tomographic images on which existence range display information is overlaid and displayed. FIG. 16A illustrates an ultrasonic tomographic image on which display information in which relative position information is added as color information to the shape of the contour of the two-dimensional existence range is overlaid and displayed. In FIG. 16A, reference numeral 601 denotes an ultrasonic tomographic image, reference numeral 602 denotes a corresponding lesion, and reference symbol S1 denotes existence range display information similar to that illustrated in FIG. 15A. Since the existence range display information S1 is overlaid on top of the ultrasonic tomographic image 601, a search region within which the actual corresponding lesion is searched for can be clearly identified. In addition, the user can easily search for the actual corresponding lesion, and an efficient search can be achieved.

By referring to the color information added to the shape of the contour of the existence range, the user can intuitively understand relative position information about the ultrasonic tomographic image 601 in the three-dimensional existence range. As in FIG. 15A, if the color information is represented in slightly light blue, it can be easily determined that the ultrasonic tomographic image 601 is located in a place near the start position 304 illustrated in FIG. 13 with respect to the three-dimensional existence range.

Figure 16B:
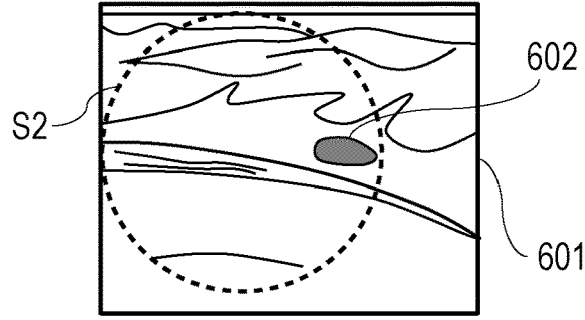
FIG. 16B is a diagram illustrating an ultrasonic tomographic image on which existence range display information is superimposed and displayed.

The existence range display information to be drawn on top of the ultrasonic tomographic image is not limited to the display information described above with reference to FIG. 16A. For example, display information in which relative position information is represented with the density of a curve representing the shape of the contour of the two-dimensional existence range may be drawn on top of an ultrasonic tomographic image. FIG. 16B illustrates an ultrasonic tomographic image on which a two-dimensional existence range in which relative position information is represented with the density of the shape of the contour is overlaid and displayed. In FIG. 16B, reference numerals 601 and 602 denote an ultrasonic tomographic image and a corresponding lesion, respectively, which are similar to those illustrated in FIG. 16A, and reference symbol S2 denotes the shape of the existence range, which is similar to that illustrated in FIG. 15B.

As can be found from FIG. 16B, by referring to the dotted line density information added to the shape of the contour of the existence range, the user can intuitively understand the relative position information about the ultrasonic tomographic image 601 in the three-dimensional existence range. If the shape of the contour is colored, the shape of the contour may be less visible as the color becomes lighter. In this case, the color representing the shape of the contour may be set to be a color of high visibility, thereby allowing the user to easily identify a dotted line even if the density of the dotted line changes. As in FIG. 15B, if a slightly coarse dotted line is used, it can be easily determined that the ultrasonic tomographic image 601 is located in a place near the start position 304 illustrated in FIG. 13 with respect to the three-dimensional existence range.

Figure 16C:
FIG. 16C is a diagram illustrating an ultrasonic tomographic image on which existence range display information is superimposed and displayed.

The color information indicating relative position information may be obtained by drawing display information in which an inner region of the two-dimensional existence range is colored on top of an ultrasonic tomographic image. FIG. 16C illustrates an ultrasonic tomographic image on which a two-dimensional existence range having relative position information drawn in an inner region thereof is overlaid. In FIG. 16C, reference numerals 601 and 602 denote an ultrasonic tomographic image and a corresponding lesion, respectively, which are similar to those illustrated in FIG. 16A, and reference symbol R1 denotes an inner region, which is similar to that illustrated in FIG. 15C.

As can be found from FIG. 16C, by referring to the color information depicted in color within the inner region of the existence range, the user can intuitively understand the relative position information about the ultrasonic tomographic image 601. In addition, coloring an inner region makes color information more visible than that obtained by coloring the shape of the contour. In this case, the inner region may be transparent enough for the user to search for the corresponding lesion 602.

Figure 16D:
FIG. 16D is a diagram illustrating an ultrasonic tomographic image on which existence range display information is superimposed and displayed.

Contrary to FIG. 16C, color information representing relative position information may be represented by drawing display information in which an outer region of the two-dimensional existence range is colored, on top of an ultrasonic tomographic image. FIG. 16D illustrates an ultrasonic tomographic image on which a two-dimensional existence range in which relative position information is drawn in an outer region is overlaid. In FIG. 16D, reference numerals 601 and 602 denote an ultrasonic tomographic image and a corresponding lesion, respectively, which are similar to those illustrated in FIG. 16A, and reference symbol R2 denotes a region, which is similar to that illustrated in FIG. 15D.

As can be found from FIG. 16D, by referring to color information in which an outer region of the existence range is colored, the user can intuitively understand the relative position information about the ultrasonic tomographic image 601. In addition, since the inner region is not colored, the user can more easily observe the inner region than the inner region which is colored, and can easily search for the corresponding lesion. In this case, the outer region may be transparent enough for the user to observe how the ultrasonic tomographic image looks in the outer region of the two-dimensional existence range.

It may be determined whether or not the tomographic image intersects the corresponding region determined in step S13050, and, if the tomographic image intersects the corresponding region, the intersection region on the tomographic image may be overlaid and displayed on top of the tomographic image.

[S13070: Combining of Tomographic Image and Cross-Sectional Image]

In step S13070, as a process of the image combining unit 1140, the information processing apparatus 1100 combines the cross-sectional image obtained in step S13040 with the image obtained in step S13060 in which the existence range of the corresponding lesion is overlaid on top of the ultrasonic tomographic image. For example, an image in which the above images are horizontally arranged side by side may be generated. Then, as a process of the display control unit 1150, the information processing apparatus 1100 displays the composite image on the display unit 1160. The composite image is also output to an external device, if necessary, through the I/F 1009, and is also stored in the RAM 1002 so as to be available from another application.

[S13080: Determination of Termination of Whole Process]

In step S13080, the information processing apparatus 1100 determines whether or not to terminate the whole process. For example, a termination instruction input by the user by, for example, pressing a predetermined key (end key) on the keyboard 1004 is acquired. If it is determined that the process is to be terminated, the whole process of the information processing apparatus 1100 ends. If it is determined that the process is not to be terminated, the process returns to step S13020, and the processing of step S13020 and subsequent steps is executed again on a new captured ultrasonic tomographic image. Accordingly, the process of the information processing apparatus 1100 is executed.

Therefore, the information processing apparatus according to this embodiment displays on an ultrasonic tomographic image a two-dimensional existence range in which relative position information about a currently displayed ultrasonic tomographic image is added, thereby allowing the user to easily determine the current position of the ultrasonic tomographic image with respect to the three-dimensional existence range while focusing on the two-dimensional existence range on the ultrasonic tomographic image. The user can therefore easily determine the degree to which the existence range to be searched remains, and can efficiently search for and identify the corresponding lesion.

Sixth Embodiment

The information processing system according to the fifth embodiment is configured to map position information about an ultrasonic tomographic image onto a color table in accordance with the start position and the end position of the three-dimensional existence range. In contrast, an information processing system according to a sixth embodiment is configured to map position information about an ultrasonic tomographic image onto a color table in accordance with position information (also referred to as a representative position, which is an example of a given position) representing a three-dimensional existence range in addition to the start position and the end position described above. The information processing system according to this embodiment has a configuration similar to that illustrated in FIG. 11, except for part of the process of the display information generation unit 1137 in the fifth embodiment. The process flow of the information processing system according to this embodiment is similar to that illustrated in FIG. 12, except part of the processing of step S13054 in the fifth embodiment. The information processing system according to this embodiment will be described, focusing on the difference from the fifth embodiment.

In step S13054, as a process of the display information generation unit 1137, an information processing apparatus 1200 according to the sixth embodiment generates display information in which relative position information is added to the two-dimensional existence range, on the basis of the shape information indicating the contour of the two-dimensional existence range, which is acquired from the three-dimensional existence range calculation unit 1135, the position information about the ultrasonic tomographic image, which is acquired from the position information calculation unit 1136, and position information representing the three-dimensional existence range. A specific generation method will be described. In this embodiment, position information representing a three-dimensional existence range will be described by using a centroid corresponding position of a three-dimensional existence range.

First, the display information generation unit 1137 sets a color table that reflects the centroid position of the three-dimensional existence range, and associates relative position information about the ultrasonic tomographic image with the color table.

Figure 14B:
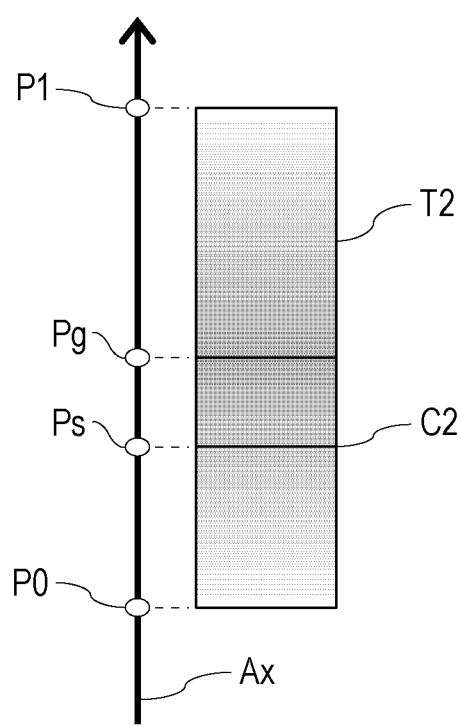
FIG. 14B is a diagram illustrating the association of relative position information with a color table.

FIG. 14B is a diagram illustrating the association between relative position information and a color table that reflects a centroid corresponding position. Reference symbols Ax, P0, P1, and Ps denote items similar to those illustrated in FIG. 13. Reference symbol Pg denotes the centroid corresponding position described above. A color table is set between the positions P0 and P1 along the axis Ax, where color continuously changes between the positions P0 and Pg and between the positions Pg and P1 in accordance with the position. Specifically, a color table is set in which the color intensity becomes reaches a maximum at the position Pg and decreases in the directions from the position Pg to the position P0 and from the position Pg to the position P1. In step S13054, color information in the color table, which corresponds to relative position information about the tomographic image corresponding position Ps normalized between the positions P0 and P1 is acquired.

Reference symbol T2 denotes a color table that reflects the position of the centroid corresponding position Pg, and reference symbol C2 denotes color information corresponding to relative position information. For example, when the color table T2 is a color table with changes in the intensity of blue and the relative position information on the tomographic image corresponding position Ps is 0.3, the tomographic image corresponding position Ps is mapped onto a position on the color table near a position of 0.5 of the centroid corresponding position Pg. Thus, the color information C2 is represented in slightly dark blue. By referring to the color information C2, the user can intuitively understand that the ultrasonic tomographic image is comparatively close to the centroid position of the three-dimensional existence range.

A color table may also be set in which different typical colors are set for the positions P0, Pg, and P1 and in which the colors continuously change among the positions P0, Pg, and P1 in accordance with the position. For example, a color table is set in which red is set for the position P0, green for the position Pg, blue for the position P1, and the colors change from red to green between the positions P0 and Pg and from green to blue between the positions Pg and P1. Thus, the user can intuitively understand which position among the positions P0, Pg, and P1 the ultrasonic tomographic image is close to. In addition, since different colors are set between the positions P0 and Pg and between the positions Pg and P1, the user can easily determine on which position P0 or P1 side with respect to the centroid position of the three-dimensional existence range the ultrasonic tomographic image is located. When the relative position information about the position Ps is 0.3, the color information C2 is represented in a color close to green between red and green. It is to be understood that a color table may also be used in which the distances between the positions P0 and Pg and between the positions Pg and P1 may be divided into a plurality of sections, each of which is assigned a different color.

Then, as in the fifth embodiment, the information processing apparatus 1200 generates existence range display information associated with the shape information on the two-dimensional existence range on the basis of the color information corresponding to the relative position information about the acquired ultrasonic tomographic image.

The position information representing a three-dimensional existence range is not limited to a centroid position. For example, when a plane parallel to the ultrasonic tomographic image 302 is translated along the orthogonal axis Ax, the position of the plane obtained when a region (two-dimensional existence range 303) where the three-dimensional existence range 301 and the ultrasonic tomographic image 302 intersect have the largest area may be determined, and a position obtained by plotting the determined position of the plane onto the orthogonal axis Ax may be used as position information representing a three-dimensional existence range.

Therefore, the user can read the degree to which the position of the ultrasonic tomographic image in the three-dimensional existence range is close to the centroid position of the three-dimensional existence range, and can more intuitively understand the position.

Modifications

The fifth and sixth embodiments described above have been described by way of example in which a three-dimensional existence range where a corresponding lesion may exist is a three-dimensional region. However, the embodiments are not limited to this example. For example, a region representing a portion of interest such as a lesion or an organ in an X-ray CT image or an MRI image may be used as a three-dimensional region. This can implemented by replacing the ultrasonic tomographic image acquired in step S13020 in the foregoing embodiments by a currently displayed slice image and further replacing the three-dimensional existence range acquired in step S13050 by a three-dimensional region of the portion of interest.

Therefore, when interpreting (or reading) an X-ray CT image or an MRI image, a doctor can intuitively understand at which position in the three-dimensional region of the portion of interest in the perpendicular direction of the slice image the portion of interest appearing in the currently displayed slice image is located. Since the degree to which the three-dimensional region of the portion of interest to be interpreted (or read) remains can be readily recognized, resulting in efficient interpretation (or reading) of the X-ray CT image or the MRI image.

Other Embodiments

The present invention may also be implemented by executing the following process: Software (program) implementing the functions of the foregoing embodiments is supplied to a system or an apparatus via a network or various storage media, and a computer (a CPU, a microprocessing unit (MPU), or the like) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. An apparatus comprising:
a memory storing a program; and
one or more processors which, by executing the program, function as:

a two-dimensional image acquisition unit configured to acquire a two-dimensional image of an object;

an existence range calculation unit configured to calculate, as an existence range, an intersection region between the two-dimensional image and a three-dimensional existence range composed of a corresponding region of a given region in a three-dimensional image of the object and an error range which is added to a circumference of the corresponding region; and a display control unit configured to cause a display unit to display, on the two-dimensional image, the existence range.

2. The apparatus according to claim 1, wherein the two-dimensional image is an ultrasonic image.

3. The apparatus according to claim 1, further comprising:

a three-dimensional image acquisition unit configured to acquire the three-dimensional image of the object, wherein the two-dimensional image is an ultrasonic image generated by capturing an image of the object using an ultrasonic probe, and wherein the display control unit is configured to cause the display unit to display a cross-sectional image of the three-dimensional image corresponding to the two-dimensional image based on a position and posture of the ultrasonic probe.

4. The apparatus according to claim 1, wherein the three-dimensional image is an MRI image or an X-ray CT image.

5. The apparatus according to claim 1, further comprising:

a coordinate transformation unit configured to perform coordinate transformation of the position of the given region from a three-dimensional coordinate system of the three-dimensional image to the three-dimensional coordinate system of the two-dimensional image; and a calculation unit configured to calculate the error range, in accordance with an error caused by the coordinate transformation.

6. The apparatus according to claim 5, further comprising:

a setting unit configured to set in the three-dimensional image a region that is larger than the given region and that includes the given region, wherein the coordinate transformation unit performs coordinate transformation of the position of the region from the three-dimensional coordinate system of the three-dimensional image to the three-dimensional coordinate system of the two-dimensional image.

7. The information processing apparatus according to claim 5, further comprising:

a specifying unit configured to specify a given portion in the two dimensional image; and a correction unit configured to correct an error in the two-dimensional image in accordance with the difference between the given portion and the corresponding region.

8. The information processing apparatus according to claim 7, wherein the display control unit causes the display unit to display a mark representing the corresponding region in such a manner that the mark is overlaid on top of the two-dimensional image in the given portion.

9. The information processing apparatus according to claim 8, further comprising:

a switching unit configured to switch an operation mode of the information processing apparatus to a mode in which when the error is corrected by the correction unit, a two-dimensional image of the object is acquired again and the existence range is not displayed on top of the acquired two-dimensional image and in which when the given portion is being displayed on top of the two-dimensional image, the mark is displayed on the display unit in such a manner that the mark is overlaid on top of the two-dimensional image.

10. The information processing apparatus according to claim 5, further comprising:

a cross-sectional image acquisition unit configured to acquire a cross-sectional image of the three-dimensional image in accordance with the position of the given region in the three-dimensional image and in accordance with the posture of the two-dimensional image, the cross-sectional image being an image that passes the given region and that corresponds to the posture.

11. The information processing apparatus according to claim 10, further comprising:

an ultrasonic probe configured to detect an ultrasonic wave from the object to acquire the two-dimensional image; and a position and posture acquisition unit configured to acquire the position and posture of the ultrasonic probe, wherein the posture of the two-dimensional image is acquired in accordance with the position and posture of the ultrasonic probe.

12. The information processing apparatus according to claim 11, wherein the display control unit causes the display unit to display an image obtained by superimposing the existence range on the two-dimensional image and an image obtained by superimposing the given region on top of the cross-sectional image.

13. An image processing method comprising:

acquiring two-dimensional image of an object;

calculating, as an existence range, an intersection region between the two-dimensional image and a three-dimensional existence range composed of a corresponding region of a given region in a three-dimensional image of the object and an error range which is added to a circumference of the corresponding region; and causing a display unit to display, on the two-dimensional image, the existence range.

14. The image processing method according to claim 13, wherein the two-dimensional image is an ultrasonic image.

15. The image processing method according to claim 13, wherein the three-dimensional image of the object is acquired, wherein the two-dimensional image is an ultrasonic image generated by capturing an image of the object using an ultrasonic probe, and wherein the display unit is caused to display a cross-sectional image of the three-dimensional image corresponding to the two-dimensional image based on a position and posture of the ultrasonic probe.

16. The image processing method according to claim 13, wherein the three-dimensional image is an MRI image or an X-ray CT image.

17. A non-transitory storage medium storing a program for causing a computer to execute an information processing method, the information processing method comprising:

acquiring two-dimensional image of an object;

calculating, as an existence range, an intersection region between the two-dimensional image and a three-dimensional existence range composed of a corresponding region of a given region in a three-dimensional image of the object and an error range which is added to a circumference of the corresponding region; and causing a display unit to display, on the two-dimensional image, the existence range.

* * * * *